(12) United States Patent
Herzog

(10) Patent No.: US 6,751,527 B2
(45) Date of Patent: Jun. 15, 2004

(54) HEAT AND MATERIAL BALANCE METHOD OF PROCESS CONTROL FOR PETROCHEMICAL PLANTS AND OIL REFINERIES

(75) Inventor: Charles Herzog, Katy, TX (US)

(73) Assignee: Stone & Webster Process Technology, Inc., Houston, TX (US)

( * ) Notice: Subject to any disclaimer, the term of this patent is extended or adjusted under 35 U.S.C. 154(b) by 415 days.

(21) Appl. No.: 09/781,913

(22) Filed: Feb. 9, 2001

(65) Prior Publication Data

US 2001/0049460 A1 Dec. 6, 2001

Related U.S. Application Data

(60) Provisional application No. 60/181,753, filed on Feb. 11, 2000.

(51) Int. Cl.⁷ .............................. G05B 21/00
(52) U.S. Cl. ............ 700/266; 700/267; 700/268; 700/270; 700/271; 700/273; 95/1; 95/16; 96/25; 210/141; 210/143; 702/22; 702/31; 702/32
(58) Field of Search ............... 700/90, 266, 267, 700/268, 269, 270, 271, 272, 273; 95/1–24; 96/25; 210/141, 142, 143; 702/22–32; 203/1–3

(56) References Cited

U.S. PATENT DOCUMENTS

| | | | |
|---|---|---|---|
| 4,230,534 A | * | 10/1980 | Stewart ..................... 203/1 |
| 4,770,841 A | | 9/1988 | Haley et al. |
| 4,956,763 A | | 9/1990 | Stewart, Jr. et al. |
| 5,249,119 A | | 9/1993 | Kaseda et al. |
| 5,640,491 A | | 6/1997 | Bhat et al. |
| 5,675,054 A | * | 10/1997 | Manley et al. ............ 585/809 |
| 5,689,032 A | * | 11/1997 | Krause et al. ............ 585/802 |
| 5,729,661 A | | 3/1998 | Keeler et al. |
| 6,111,156 A | * | 8/2000 | Oballa et al. ............. 585/330 |
| 6,141,988 A | * | 11/2000 | Engler et al. .............. 62/624 |

OTHER PUBLICATIONS

WO 01/59534 A1, Herzog, Heat and Material Balance Method of Process Control for Petrochemical Plants and Oil Refineris, Aug. 16, 2001.*

* cited by examiner

Primary Examiner—Ramesh Patel
(74) Attorney, Agent, or Firm—Hedman & Costigan, P.C.

(57) ABSTRACT

A method comprising:
  a) selecting a loading variable from operating variables, the loading variable being directly related to total energy input into the system and equipment constraint of the system;
  b) selecting a performance specification variable which is required to be kept within a defined target at all times during operation of the system; and
  c) pairing the performance specification variable with a manipulated variable having a mass/balance relationship to the performance specification which is not the loading variable and;
  d) controlling the manipulated variable to maintain the performance specification variable with the defined target.

13 Claims, 20 Drawing Sheets

HMB STRATEGY: CONSTRAINED CONTROL OF ETHYLENE PURITY

FIG. 1  HMB STRATEGY: CONSTRAINED CONTROL OF ETHYLENE PURITY

BACK END AC CONVERTERS WITH CONVENTIONAL RATIO CONTROL

BACK END AC CONVERTERS
WITH RATIO-ASSISTED
CONTROL

FIG. 8  ADVANCED LEVEL CONTROL WORKING WITH RATIO ASSISTED CONTROL

CAPACITY MAXIMIZATION STRATEGY

DISTILLATION SYSTEM PROCESS FLOW DIAGRAM
PROCESS FLOW DIAGRAM HIGH PURITY DISTILLATION SYSTEM

LIGHT ENDS TOWER BASIC REGULATORY CONTROL STRATEGY

FEED RATE INCREASE AND OPERATORS' RESPONSE

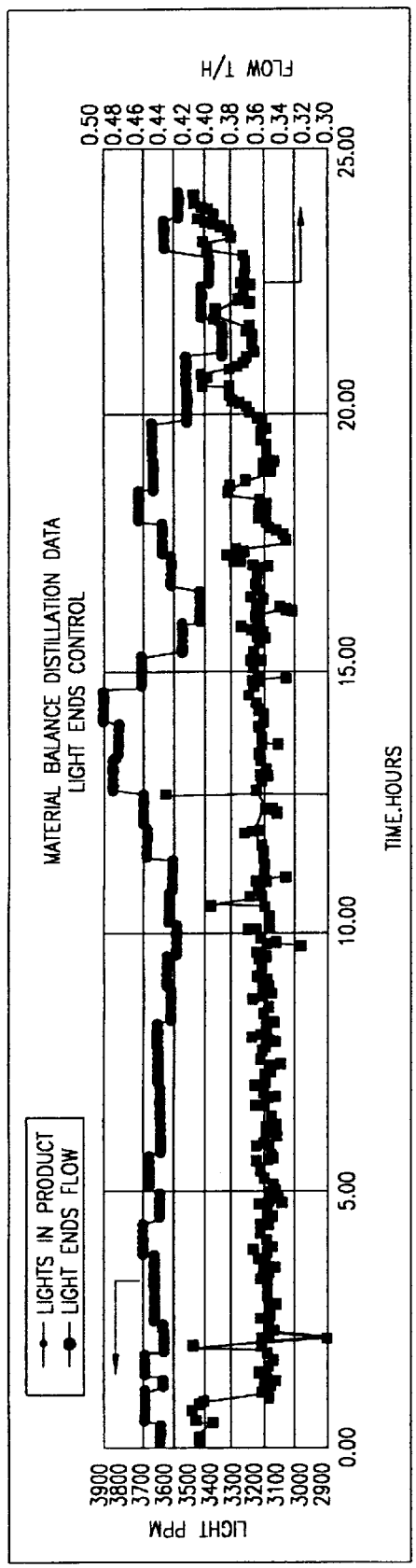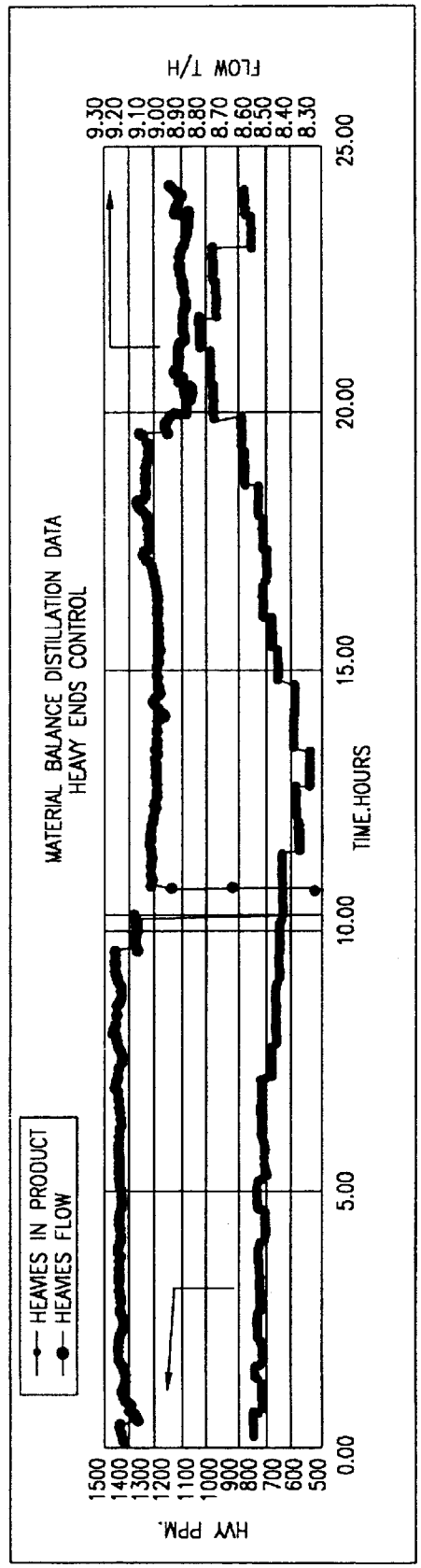

HEAT AND MATERIAL BALANCE METHOD OF PROCESS CONTROL FOR PETROCHEMICAL PLANTS AND OIL REFINERIES

The present application is a continuation in part of U.S. Provisional Application Serial No. 60/181,753, filed Feb. 11, 2000.

FIELD OF THE INVENTION

The present invention relates to the field of chemical process control and in particular the field of ethylene plant control.

BACKGROUND OF THE INVENTION

Chemical processes such as those run in petrochemical plants must be precisely controlled in order for the processes to run efficiently and economically. Various strategies have been used to facilitate process control of individual systems and to coordinate and integrate multiple systems within a plant operation. Multivariable controllers have been commonly used in petrochemical plants for high-level control functions including distillation control, furnace severity capacity enhancement as well as other applications involving rigid product quality specification and constrained operation.

The use of multivariable controllers in the operation of these plants however, has a number of significant disadvantages. Multivariable controllers are based on complex dynamic models, solved by proprietary software packages that run on expensive host computer systems. Continued operation of these platforms requires investment in computer specialists, hardware and software upgrades, and permanent advanced control maintenance staff, who are specially trained in the use of multivariable control software.

Another disadvantage of the multivariable control strategy is that the multivariable controller causes an oscillation effect in the chemical process after a disturbance. The oscillation is a result from the tendency of the multivariable controller to push the chemical processes directly against equipment constraints or performance specifications in the short term. Consequently, the processes are often run with a small gap between the average operating point and the limit when a disturbance occurs. For many variables such as distillation product purity, there is not sufficient time to wait for feedback information before acting. The requirement for fast action combined with even a small model error can result in an oscillating process that is inefficient.

Another disadvantage of multivariable control strategy of moving quickly to respond to disturbances or to maximize the objective function leads to unsteady flows and inventories within large systems, preventing the equipment from operating at maximum efficiency. This may lead to a system appearing constrained when it simply needs to become steady to achieve its performance specification.

Another disadvantage of the multivariable control strategy is that the basic control of product specifications are run under constrained conditions. Basic regulatory control systems are characterized by the one-to-one pairing between controlled variables and manipulated variables. Some of these parings are configured as automatic control loops, while others are under control of the operator. For example, in traditional systems a manipulated variable such as internal reflux may be paired with ethylene purity, a controlled variable.

With this strategy, the operator increases reflux to improve the ethylene purity while the reboiler achieves the heat balance with the tray temperature controller. The strategy keeps both product compositions near target until a constraint is reached. Under constrained operation, the operator can no longer increase reflux to maintain ethylene product purity. The only remaining choices are to lower temperature target or to reduce feed. If the operator decides to lower the temperature, then the control problem changes and becomes more complex.

Ethylene purity becomes the outer loop of a cascade, with tray temperature control being the inner loop. This is not an effective cascade because of the long time constant of temperature control to effect a change in ethylene purity and non-linearity of the gains.

Dynamics are not the only problem with the conventional multivariable controller strategy. For multivariable controller strategy to be successful at both maximizing the capacity of the tower and approaching steady state operation, the precise temperature target must be identified such that the limits of both product purity and equipment capacity are reached at a given reflux rate. Stated another may, the reflux rate and the heat, which are both manipulated variables, must be set so that dependent variables such as temperature, ethylene purity, and constraint are all controlled simultaneously.

Tray temperature had traditionally been considered the most important regulatory control variable and many multivariable control applications continue to keep the temperature controller in service while the computer manipulates its target. Also, it can become quite difficult to identify the correct temperature setting as feed composition and tray efficiency varies over time.

When a multivariable controller is configured with the tray temperature controller in service, there is a constant struggle to find just the right temperature that satisfies the product specification and the objective function simultaneously. Even the slightest model error can cause the multivariable controller to move the temperature target up and down trying to find the precise solution to the over-defined problem with a low controller as the inner loop of the cascade. As the temperature controller wanders, so does the entire plant with it, beginning with the recycle ethane flow.

With the conventional multivariable controller strategy, recycle ethane flow is continually being moved to control the bottoms level. Whenever the reflux is adjusted for ethylene purity control, there is a corresponding response from the tray temperature controller. As this adjustment proceeds, any imbalance between the reflux and the heat appears as a change in the level of the bottoms, which, in turn, requires a response from the relatively small recycle ethane flow. A small percentage error between the reflux and the heat demands a relatively large percentage change in ethane flow via the bottoms level controller.

The problem for the conventional strategy is even more difficult during constrained operation. When the tower becomes constrained and the temperature target is adjusted to control ethylene purity, the likelihood of recycle ethane flow oscillation is increased. As ethylene purity is pushed closer to the limit this effect becomes more pronounced.

If the recycle ethane flow does begin to oscillate, the capacity of the vaporizer can be exceeded at the peaks of the oscillation cycles, causing material to "back up" into the splitter bottom. When this happens, the operator is powerless to remedy the situation. His only recourse is to cut feed so that the peak recycle ethane can be vaporized.

The speed of the computer in performing dynamic calculations cannot eliminate these fundamental problems relating to moving inventory up and down the tower.

Another disadvantage of the multivariable controller strategy is that it does not provide an adequate integrated response to a disturbance such as changes in the fluid levels of vessels used in the plant. Stewart Jr. et al., U.S. Pat. No. 4,956,763 describes a devices that controls surge levels in vessels used in petrochemical plants by neutron backscatter which allows personnel to respond to disturbances in a control variable, such as the flow rate of liquid feed, in order for the plant to operate safely and efficiently. However, the device only detects the liquid level in a vessel and adjusts the inlet or outlet flow to compensate for incoming surges; it does not address disturbances such as changes in feed composition or feed flow rate.

A new method for achieving high-level advanced control of petrochemical processes without complex dynamic models or host computers is needed.

SUMMARY OF THE INVENTION

Accordingly, an improved method for controlling a chemical processing system having a plurality of operating variables is disclosed in the present invention having operating variables, the method comprising:

(a) selecting a loading variable from the system operating variables, the loading variable being directly related to total energy input into the system and equipment constraint of the system;

(b) selecting a performance specification variable which is required to be kept within a defined target at all times during operation of the system; and (c) pairing the performance specification variable with a manipulated variable having a mass or heat balance relationship to the performance specification and which is not the loading variable; and (d) controlling the manipulated variable to maintain the performance specification variable with the defined target.

DETAILED DESCRIPTION OF THE INVENTION AND DESCRIPTION OF THE PREFERRED EMBODIMENTS

Much of the detailed description that follows is directed to control of a C2 splitter. This is done for the sake of simplicity and should not be construed as a limitation of the present invention which is applicable to a wide variety of chemical process systems.

Figure 1:
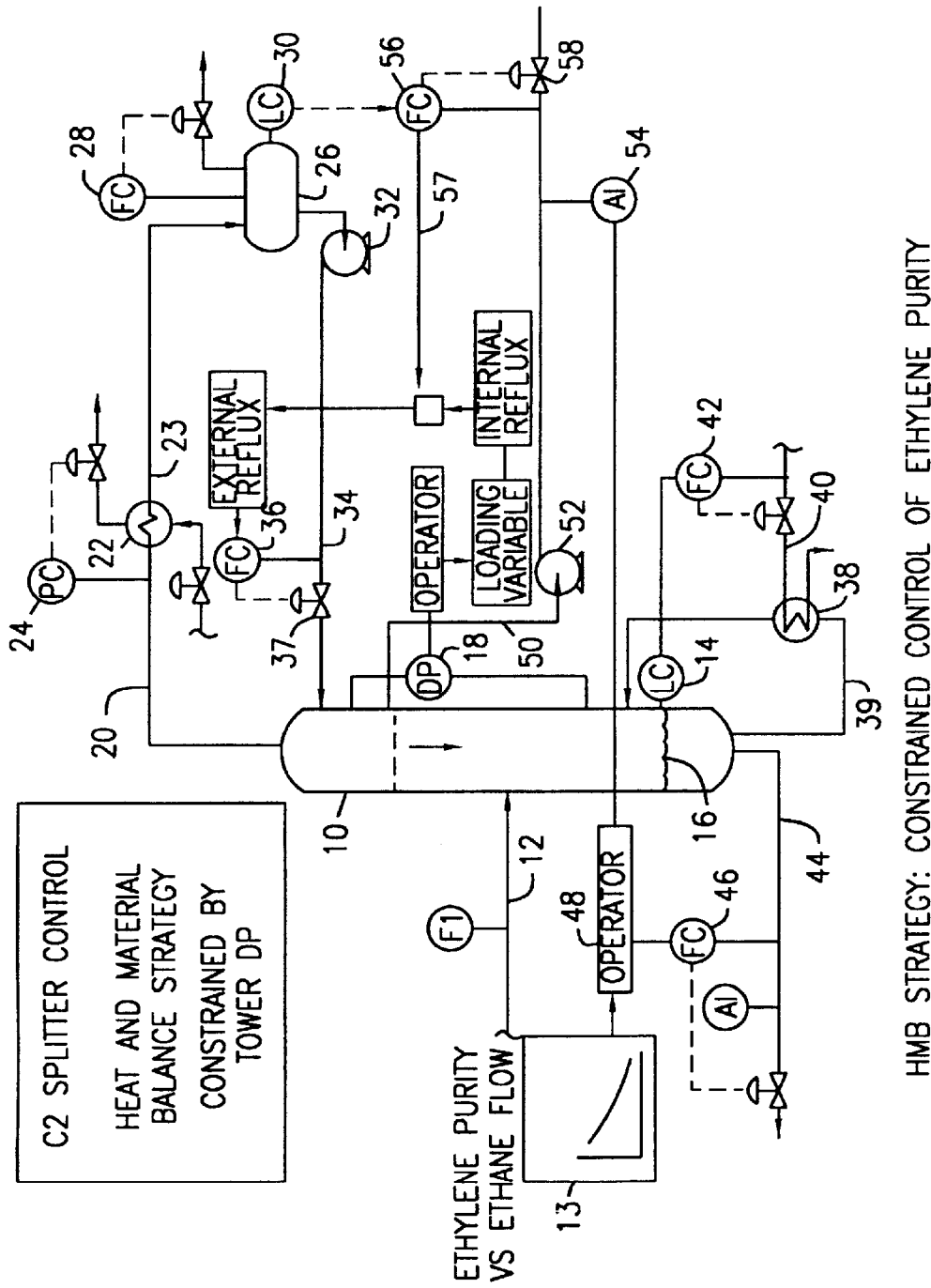
FIG. 1 is a schematic diagram of the splitter process of the present invention.

FIG. 1 is a diagram of an ethylene splitter system using a control system of the present invention showing a continuous column distillation tower 10 and demonstrates the loading variable concept of control. Feed, which is typically comprised of a mixture of ethylene and ethane, is introduced into the central portion of the distillation tower 10 through a feed input line 12. A level controller 14 is used to control the level of bottoms 16 in the lower portion of the distillation tower 10. An internal reflux controller 18 is connected between the lower portion and upper portion of the distillation tower 10. Vapor is withdrawn from tower 10 through a vapor withdrawal conduit 20 and is directed to a heat exchanger 22. A vapor pressure controller 24 controls the flow of coolant to the heat exchanger 22 that partially condenses the vapor.

The partially condensed vapor in a line 23 is feed to a drum 26. A drum level controller 30 is used to measure the level of liquids in the drum 26. A vapor flow controller 28 is used to control the vapor flow exiting the drum 26 which information is fed to a flow controller 56 which controls product flow via a valve 58 and provides information via a line 57 which is combined with information from internal reflux controller 18 to an external reflux controller 36 described more particularly herinbelow. Liquid is removed from drum 26 via pump 32 and returned to tower 10 as external reflux via a conduit 34. A flow controller 36 controls the flow of the external reflux conduit 34 via a valve 37. The information from internal reflux controller 18 is set as the loading variable. This variable is directly related to the amount of energy input into the system, i.e., cooling required to condense the ethane. The loading variable is held constant or nearly constant in the short term operation, thus keeping a relatively constant load on the equipment and thereby steadying the process. However, when the system equipment is constrained by mechanical limitations, then the loading variable can be slowly adjusted to maintain a steady operation near the system limits. The loading variable is not manipulated to control a product specification, such as ethylene purity in a C2 splitter. Instead, it is dedicated solely to the control of the most limiting equipment constraint.

A reboiler exchanger 38 is connected to the lower portion of the tower via a line 39. Heating steam to exchanger 38 is supplied via a line 40 and a flow controller 42 receiving bottoms level information from bottoms level controller 14 controls the flow of steam to the exchanger 38. Ethane is removed from the tower 10 via a line 44 which is controlled with a flow controller 46. Thus, the operator 48 directly controls the ethane flow in line 44 according to preestablished ethylene purity/ethane flow correlation 13 for the system. Ethylene product is removed from the top tray of tower 10 via a product line 50.

In operation, a feed mixture is passed through the feed input line 12 and into the middle portion of the tower 10. The distillation tower 10 may be equipped with a series of vertically stacked trays or plates. Liquid flows down the tower 10 where it is collected in the bottom of tower 10. A portion of the liquid is withdrawn via line 39 for feeding to a reboiler exchanger 38 which supplies heat to vaporize the liquid. The vapor from the reboiler 38 is re-introduced into the tower 10 via a line 58.

Figure 2:
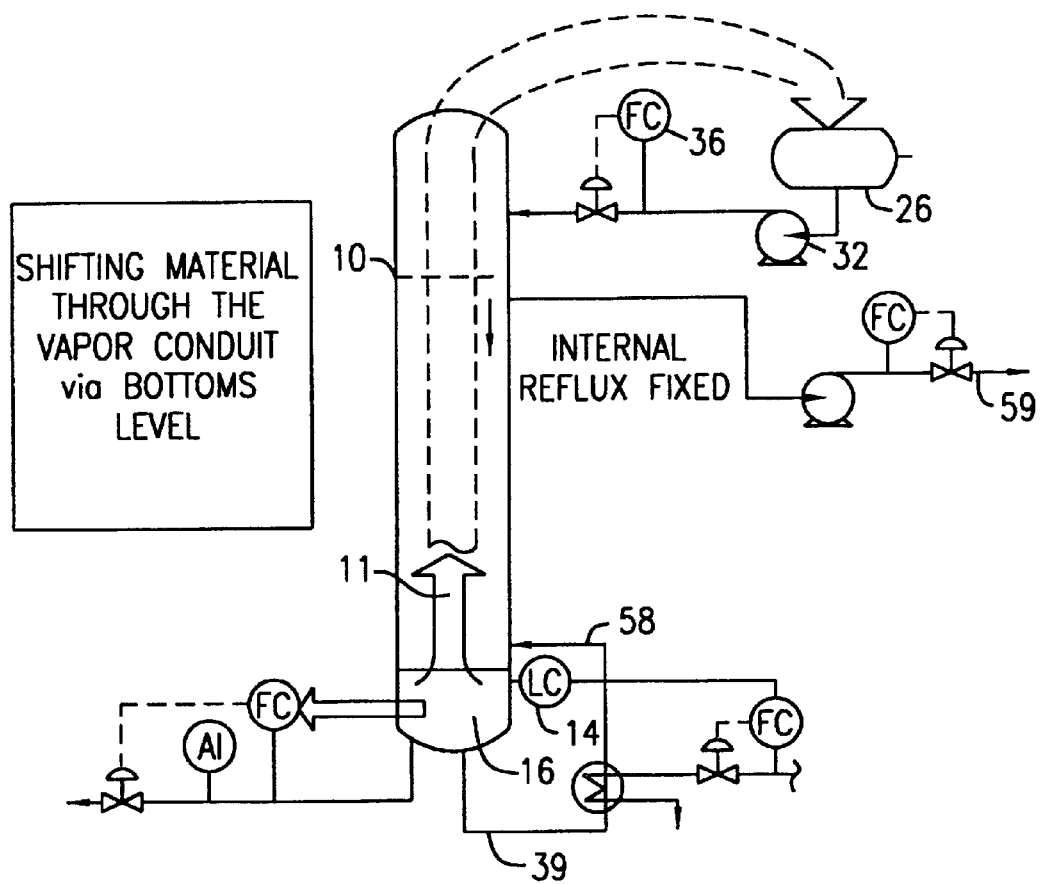
FIG. 2 is a schematic diagram of the present invention showing the shifting of material through the vapor conduit.

FIG. 2 exemplifies how material can be moved in tower 10 through the vapor conduit 11 via the level of the bottoms 16. The material, typically a mixture of ethane and ethylene, moves from the bottoms portion 16 of the tower 10 and up through the tower to reflux drum 26. Because the internal reflux is fixed as a loading variable, by material balance principles, decreasing the vapor flow (i.e. raising bottoms level) will necessarily result in an increase in ethylene purity in product stream 59.

It has been surprisingly found that controlling the chemical process by using heat and material balance in accordance with the present invention significantly improves the performance of chemical processes such as petrochemical processing and ethylene splitting. Table 1 shows manipulated and controlled variables that apply for the single loop, operator's basic regulatory control version of the heat and material balance strategy for a C2 splitter.

TABLE 1

| Manipulated Variables | Controlled Variables |
| --- | --- |
| 1. Ethylene Product Rate | Reflux drum level |
| 2. Recycle Ethane Rate | Ethylene purity (by operator) |
| 3. Internal Reflux | Loading Variable (By operator) |
| 4. Reboiler Duty | Bottoms level (by operator) |
| 5. Condenser | Pressure |

The material balance strategy for C2 splitter constrained control can be identified by the following characteristics:
1. Control of ethylene product quality is achieved by reducing system load.
2. Tower 10 is heat balanced via bottom level rather than by tray temperature.
3. Loading variables are used to manage constraints and utility consumption.
4. Neither temperature nor recycle ethane is directly controlled.

Loading Variable as a Constraint Management and Utility Control Optimization Tool The loading variable, as the name implies, is an independent manipulated variable. The loading variable is usually associated with an external source of energy to the system such as fuel, cooling, or electrical power. The concept of loading variables is that the loading variable is held constant or nearly constant in the short term. This keeps constant load on the equipment and generally steadies the process.

This basic regulatory control strategy is specifically designed to manage constraints. Constraint management has heretofore been the domain of the multivariable controllers.

If the tower 10 is not constrained by the equipment, then the cost associated with the loading variable is evaluated against a profit-related variable such as recycle ethane purity. With the system acting at steady state, the evaluation is easy to perform. If the operator decides to change the setting of the loading variable, the loading variable is ramped towards the new target very slowly. This ensures that the system transitions smoothly to a new steady state without disturbing the inertia of the system.

Every system within the ethylene plant has at least one suitable loading variable. There may be more than one suitable loading variable in a system. In most systems, there is a single dominant loading variable that affects the energy input into the entire system.

Table 2 gives examples of loading variables for other areas in the ethylene plant.

TABLE 2

| Ethylene Plant System | Loading Variable |
| --- | --- |
| Furnace | Firing duty |
| Compressor | Speed or steam flow |
| Compressor | Speed or steam flow |
| Depropanizer | Reboiler Duty |

It is anticipated that loading variables for other chemical process systems can readily be identified by those of ordinary skill in the art based on the detailed description herein.

The loading variable is used together with the performance specification variable to complete the objectives of high purity constrained control.

Performance specification variables are defined as dependent process variables that must be kept at a precise target or within a certain limit at all times. While many variables are treated in industry as performance specification variables, there are only a handful of variables that can truly be considered as performance specification variables according to the above definition.

Multivariable controllers tend to treat all dependant variables as performance specification variables. Every available degree of freedom is continually moving to control some dependent variable or maximize the objective function. This movement, especially in the typical multivariable control time horizon, results in a process that appears never to reach steady state.

Many systems in the ethylene plant do not have a true performance specification variable, such as the cracking furnace. While cracking severity is a very important profit-related variable, there is no urgency to move fuel and other variables quickly to achieve a given severity target. What really matters is the average severity and steady operation. Table 3 shows an example of performance specification variables in the ethylene plant.

TABLE 3

| Ethylene Plant System | Specification Variable |
| --- | --- |
| C2 splitter | Ethylene in Ethylene Product |
| AC/MAPD Converter | AC/MAPD in Converter Effluent |
| Drier Feed Converter | Outlet Temperature |
| C3 Splitter | Propane in Propylene Product |
| Caustic tower | H2S/CO2 in Effluent Process Gas |

Each performance specification variable is paired with a single manipulated variable. This manipulated variable is called the controlling manipulated variable, must be free to complete its task, unimpeded by equipment constraints. The constraints are addressed by the loading variable.

In the regulatory configuration, the variable controlling the ethylene purity is recycle ethane flow. The operator increases ethane flow at the tower bottom to improve ethylene purity. The change in ethane flow accomplishes two things. First, additional moles of ethane are taken out of the system immediately, directly affecting the component material balance. Second, the vapor rate in the tower 10 decreases via the level of the bottoms 16 after the ethane flow is increased.

Thus, the purity is controlled as the process moves away from the existing constraints. The strategy always works regardless what constraint is active in the splitter system.

Accordingly, under the control system of the present invention the operator learns a single strategy, which can be applied at all times. The advanced control system applies the identical strategy, but also automates some of the operator's tasks in the regulatory configuration. This consistency between regulatory and advanced control methods is lacking with traditional multivariable control systems.

Maintaining the steadiness of the loading variable over time is important to using heat balance control. When reflux is held constant, vapor flow up the tower 10 may be thought of as a conduit for moving material from one the end of the tower 10 to the other. See FIG. 2. Direct and instantaneous control of the material passing through the conduit can be accomplished by using the material balance of control.

What makes the control system of the present invention strategy so easy to implement is that the tower 10 is heat balanced through the level of the bottoms 16 instead of the tray temperature. The bottoms level is a good indicator of heat and material balances being satisfied, and its gain against the reboiler duty is constant and known from the dimensions of the tower 10.

Another significant advantage of heat and control system of the present invention material balance is that recycle ethane flow is kept nearly constant at all times which permits the heat exchanger to operate at constant duty, allowing close approach to the exchanger limit. The ability to operate the heat exchanger in this fashion is directly related to ethylene plant capacity in many ethylene plants. This is especially true in ethane crackers where peaks in recycle ethane flow result in reduced furnace capacity for fresh feed.

With the conventional multivariable control strategies, recycle ethane is constantly being moved to control the bottoms level. Whenever the reflux is adjusted for ethylene purity control, there is a corresponding response from the tray temperature controller. As this adjustment proceeds, imbalances between the reflux and heat appear as a change in bottoms level, thus requiring a response from the relatively small recycle ethane flow. Accordingly, a small percentage error between the reflux and the heat demands a relatively large percentage change in ethane flow via the bottoms level controller.

These problems for conventional control systems are further exacerbated during constrained operation. When the tower becomes constrained and the tray temperature target is adjusted in response to control ethylene purity, the likelihood of recycle ethane flow oscillation is increased. As ethylene purity is pushed closer to the desired limit this effect becomes more pronounced. Furthermore, if recycle ethane flow begins to oscillate, the vaporizer capacity can be exceed at the oscillation cycle peaks, causing material to back up into the splitter bottom. When back up occurs in this manner, the only option for the operator to remedy the situation is to cut the feed rate so that peak recycle ethane flow can be vaporized.

Figure 3:
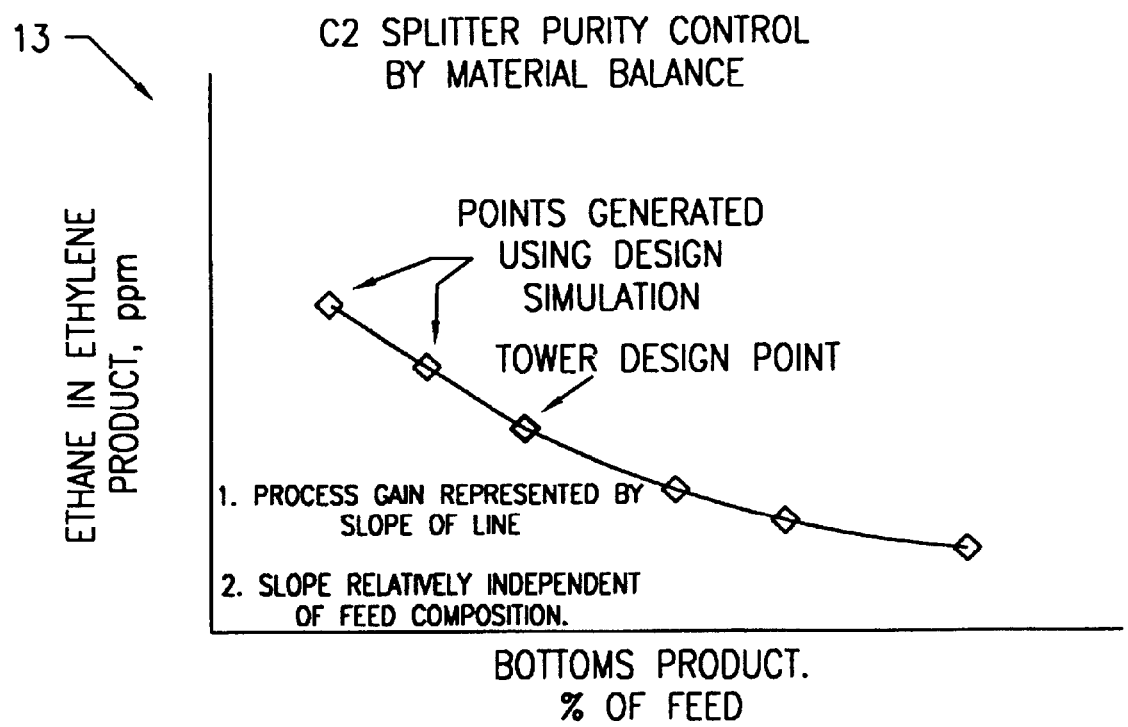
FIG. 3 is a graph showing ethylene purity control using the present invention.

Process design data techniques can be used in the control of performance specification variables. Existing steady-state design simulations can be used to determine approximate process gain between recycle ethane flow and ethylene purity in a correlation graph 13 (FIG. 1). Referring to FIG. 3 there is shown a more detailed graph 13 showing a typical relationship between recycle ethane flow and ethylene purity that might be generated by a simple plot of simulation output. The slope of the plot gives the approximate process gain. The plot in FIG. 3 is nearly a straight line because the strategy directly shifts moles of ethane from one end of the tower 10 to the other end. The composition change is always directly proportional to the numbers of moles shifted. A graph similar to FIG. 3 can be posted in the control room or configured in a DCS block for a higher-level advanced level of control application.

By comparison, under the conventional multivariable strategy, dynamic models of both reflux tray and temperature (or recycle ethane purity) against ethylene purity are needed. These models are highly non-linear, making them less robust then material balance models. Many outside factors including feed composition and tower efficiently can also affect the multivariable controller gains.

Another advantage of the heat and material balance strategy of this invention is that the process control configuration can be easily changed if new equipment is added to the system, such as in debottlenecking projects. The activities of configuring the modified control system, and determining the new process gain, are carried out simultaneously with the process design activities. This accomplishes the retrofit of the heat and balance control system at consequential cost.

For example, assume that a smaller pre-splitter is installed upstream of the existing C2 splitter to reduce traffic and relieve flooding of the existing tower. All that is required is to use the material balance process control tools of the present invention, such as ratio-assisted control (described more fully hereinbelow), on the pre-splitter is to graph the recycle ethane flow against ethylene purity with the new simulation.

Another aspect of the invention is that advanced regulatory strategy can be used to automatically respond to feed rate change. A specific strategy for handling feed rate changes is paramount in the ethylene plant because furnaces are switched so frequently. The ability of the control system to keep products on specification during a feed change determines whether long term control and optimization objectives will be achieved.

The advanced regulatory layer of heat and material balance control comprises of tools specifically designed to accommodate feed rate change during furnace switch. Two different control method tools which can be used can be used in the practice of the present invention are ratio-assisted control and advanced level control.

Ratio-assisted controls are tools that are used to maintain heat and material balances on complex systems during feed rate change. The control of most dependent variables in an ethylene plant can be facilitated by ratio-assisted controls.

Figure 4:
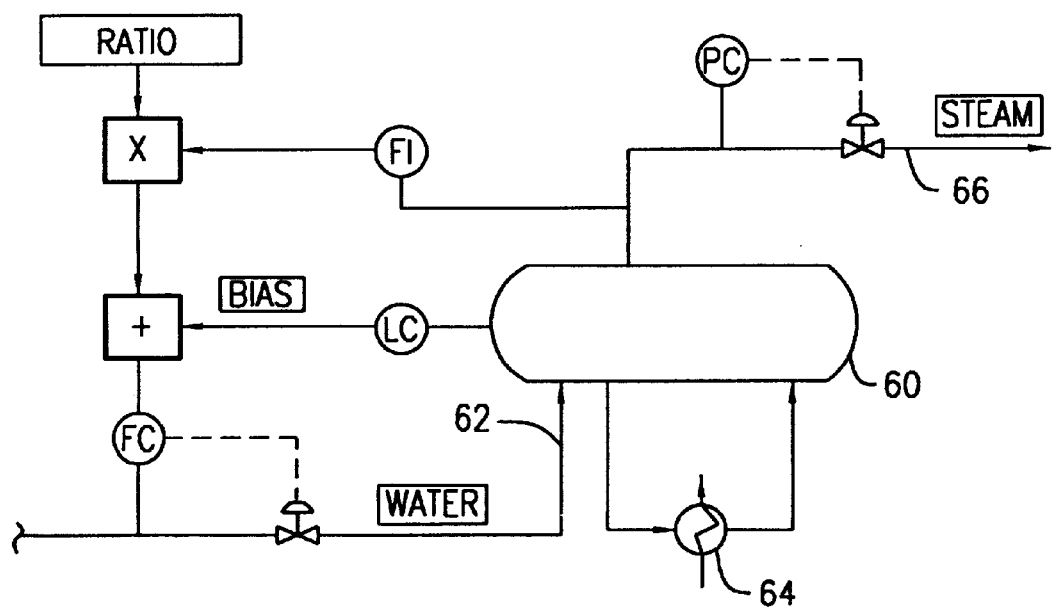
FIG. 4 is a schematic diagram of steam drum level control using the present invention.

One of the most common examples of ratio-assisted controls is a three point control for steam drums. Referring to FIG. 4, there is shown a diagram of a steam drum level control apparatus. In FIG. 4 water is added to a steam drum 60 via a line 62. The water is heated via exhanger 64 to produce steam which exits steam drum 60 in a line 66. Control of the level of the water in the steam drum is effected by regulating the amount of water entering the steam drum 60 in ratio to the stream produced. The water flow is then biased as necessary to control the level.

The basic equation for the stream drum application is:

$$\text{Water Flow} = \text{Ratio} \times \text{Steam Flow} + \text{Bias}$$

In this case the ratio is nearly 1.0 if mass units are used for both water and steam. The bias represents some function of level, usually calculated from a PID general control equation. Advanced level control can also be used to set the bias on the level controller.

The use of ratio-assisted control of the steam drum greatly reduces the error that must be addressed by the primary level controller. When the steam production varies, the resulting change in level is smaller than it would be without the assistance from the ratio control. This means that tuning can be set very conservatively, while still resulting in tight control of the level. The same principle applies to virtually all controllers. Ratio assisted control can be installed directly on the DCS for almost any system where energy and mass flows can be measured. The task of any feedback control loop becomes easier because of smaller initial error.

Binary distillation is an example for ratio-assisted control. In the C2 splitter, ratio-assisted controls can be applied on all four major manipulated variables as follows:

Manipulated Variable Target=Ratio×Feed+Bias

Table 5 gives the specific configuration of the ratio-assisted manipulated variables.

TABLE 5

| Ratio-Assisted Manipulated Variables | Controlled Variables |
|---|---|
| Ethylene Product Flow | Reflux Drum Level |
| Recycle Ethane Flow | Ethylene Product Purity |
| Internal Reflux | Constraint Control or Utility Optimization |
| Reboiler Duty | Bottom Level |

The performance of ratio-assisted controllers is more consistent than that of straight ratio controllers, because the primary controllers listed in Table 5 adjust only the bias of the ratio-assisted controller, not the ratio. As a result, the ratio targets can be permanently set by the operations team to reflect design heat and material balance relationships.

In the advanced control configuration, the ratio used for the recycle ethane flow calculation is based on the product of feed rate multiplied by ethane concentration in the feed. This gives heat and material balance control a direct method to respond to feed composition change without non-linear composition model.

Figure 5A:
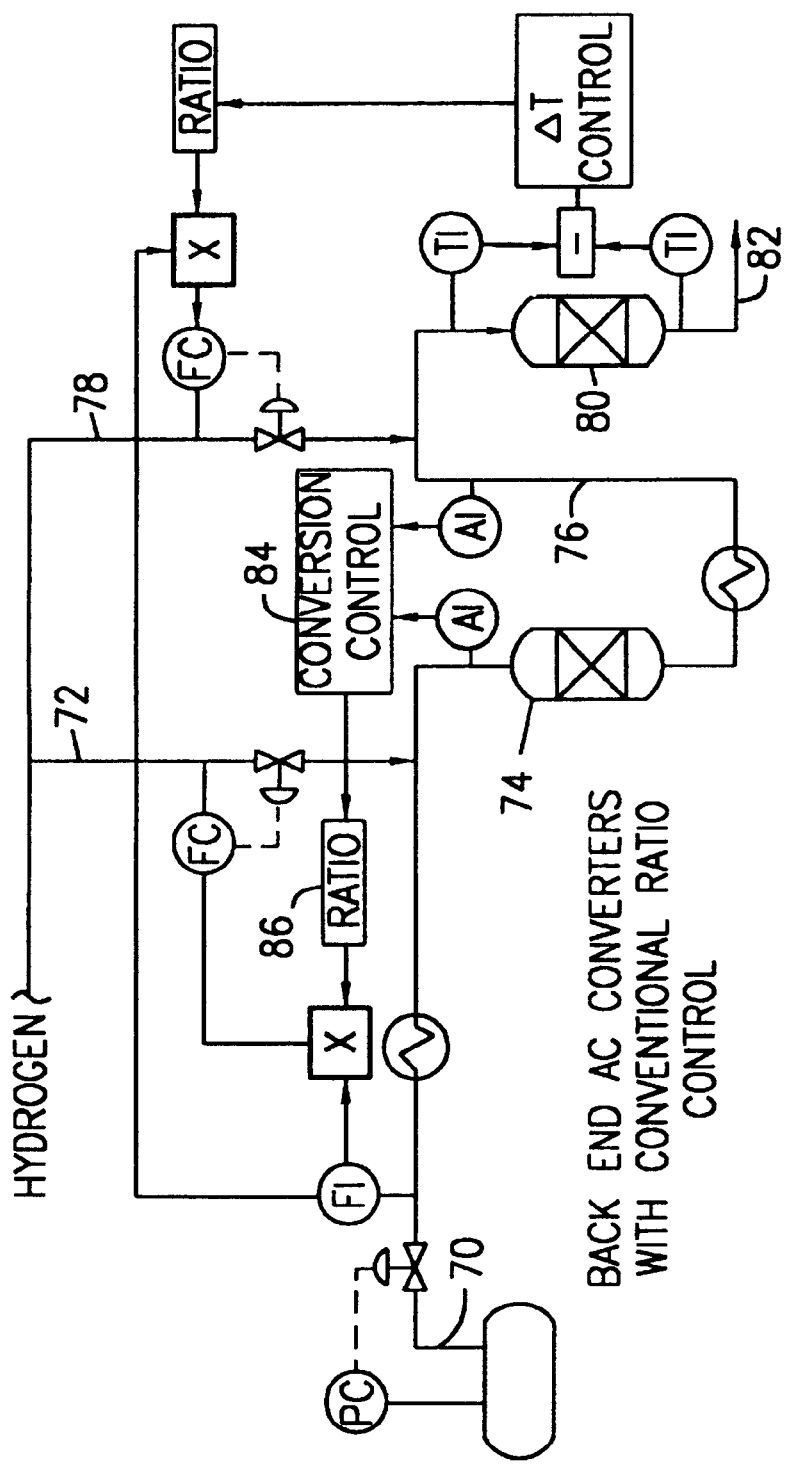
FIGS. 5a and 5b are schematic diagrams of a back end AC converter using the present invention with ratio assisted control.

Back end acetylene converter control provides another example of the advantages of ratio assisted control over direct ratio control. Referring to FIG. 5A, there is shown a back end acetylene conversion system with conventional ratio control. A feed stream containing acetylene in a line 70 is combined with hydrogen from a line 72 and fed to a first bed reactor 74. Partial conversion is effected in reactor 74 and the partially hydrogenated effluent exits the first reactor in a line 76. Additional hydrogen is added to the effluent from the first reactor via a line 78 and fed to a second reactor 80. The converted effluent is removed from the second reactor 80 in a line 82 for further down stream processing. In this type of prior art system, acetylene conversion 84 in the first bed reactor 74 is controlled in a cascade with hydrogen-to-feed ratio control 86. In these systems the hydrogen ratio target is continually being changed. Thus, when a feed change does occur, the quantity of hydrogen added depends of the current value of the ratio target. The ratio target does not remain the same from one feed change to the next, or even during a given feed change.

Figure 5B:
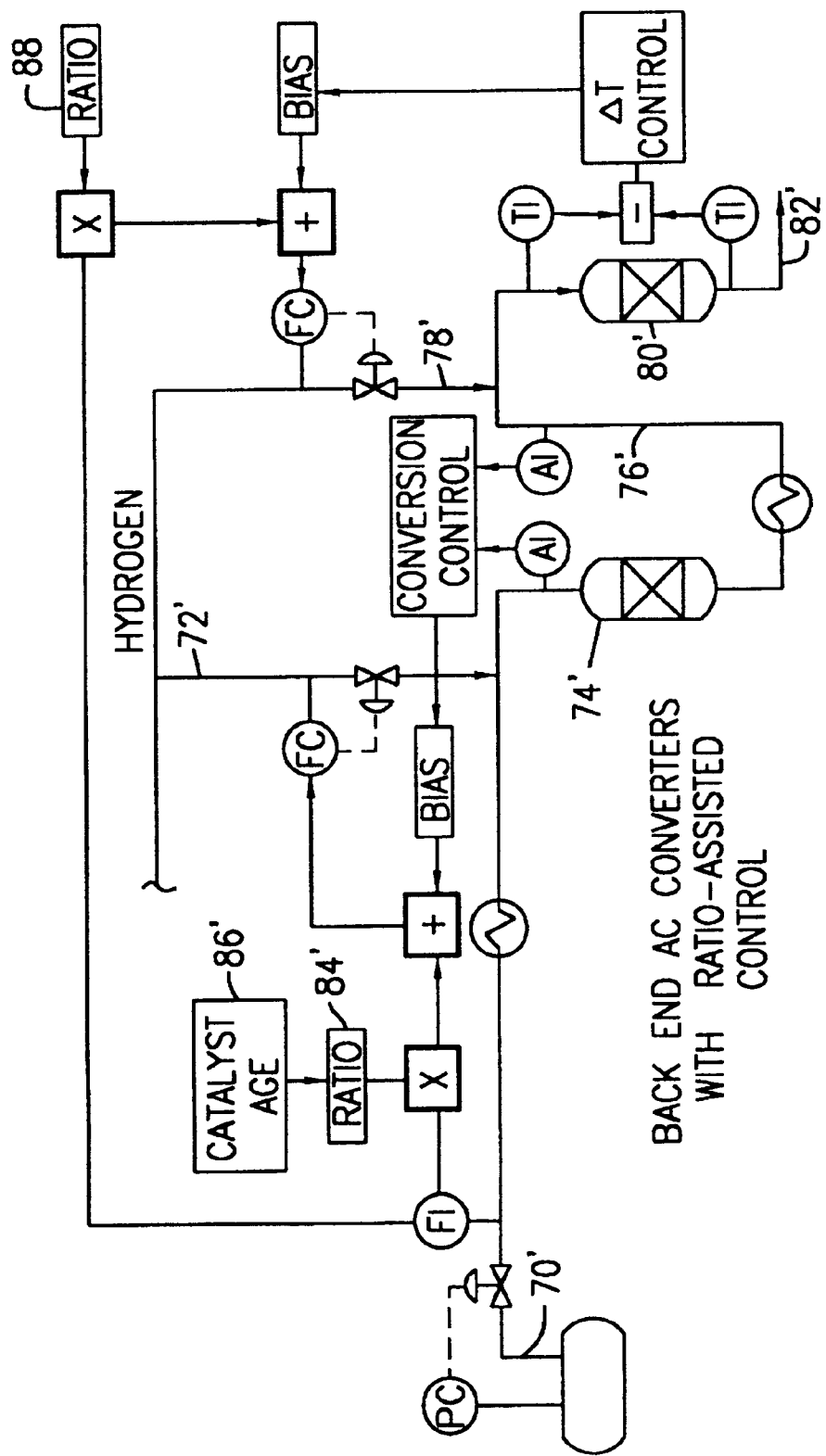

FIG. 5B shows a back end acetylene converter as commonly used in the art implemented with ratio assisted control of the present invention where the ratio target 54 is set to reflect the current condition of the catalyst 86 and is not changed in the short term. The target can be changed either manually, or automatically, as the online catalyst bed ages. Now, when the feed change occurs, the corresponding change of hydrogen is completely repeatable and predictable as well as adjusted for catalyst condition. The ratio can also be adjusted automatically to account for any changes in acetylene content of the feed system 88. If the feed analyzer is out of service, then the control remains in service assuming constant feed composition.

Maintenance of the back end converter application with ratio-assisted control is as simple as changing the ratio target. Any process engineer or DCS engineer normally assigned to the unit can make the changes without any special software training. This is important for high maintenance controllers such as acetylene converters, whose performance varies through time and susceptible to sudden changes when a new catalyst bed is put on line.

By comparison, to change the multivariable control to reflect changes in catalyst performance requires a specialist in the multivariable control software, especially for a sensitive application such as acetylene converters.

The use of ratio-assisted controls in the acetylene converter application eliminates the need for a multivariable controller. The load changes are handed directly by the ratio, leaving the conversion control bias with only a small error to address. Ratio-assisted controls give their best results if the feed changes to a system are gradual and without oscillation. Ratio assisted controllers can use predictions of the feed to the system instead of the measured feed to handle transitions. These predictions, as well as steady feed, are provided by advanced level control. This allows more time for the manipulated variables to change, leading to more gradual and steady approach to the new opening target.

Advanced Level Controls

Advanced level control as referred to herein is defined as the use of level measurement and vessel dimensions to control accumulations and material imbalances directly. The magnitude of a feed change to a vessel can be calculated from the rate of change of level and vessel dimensions. Once the magnitude of the feed change is known, the following are directly calculated.

1. Magnitude of change in product rate required before constant level is established.
2. Accumulation between current time and time at which constant level is reached.

Figure 6:
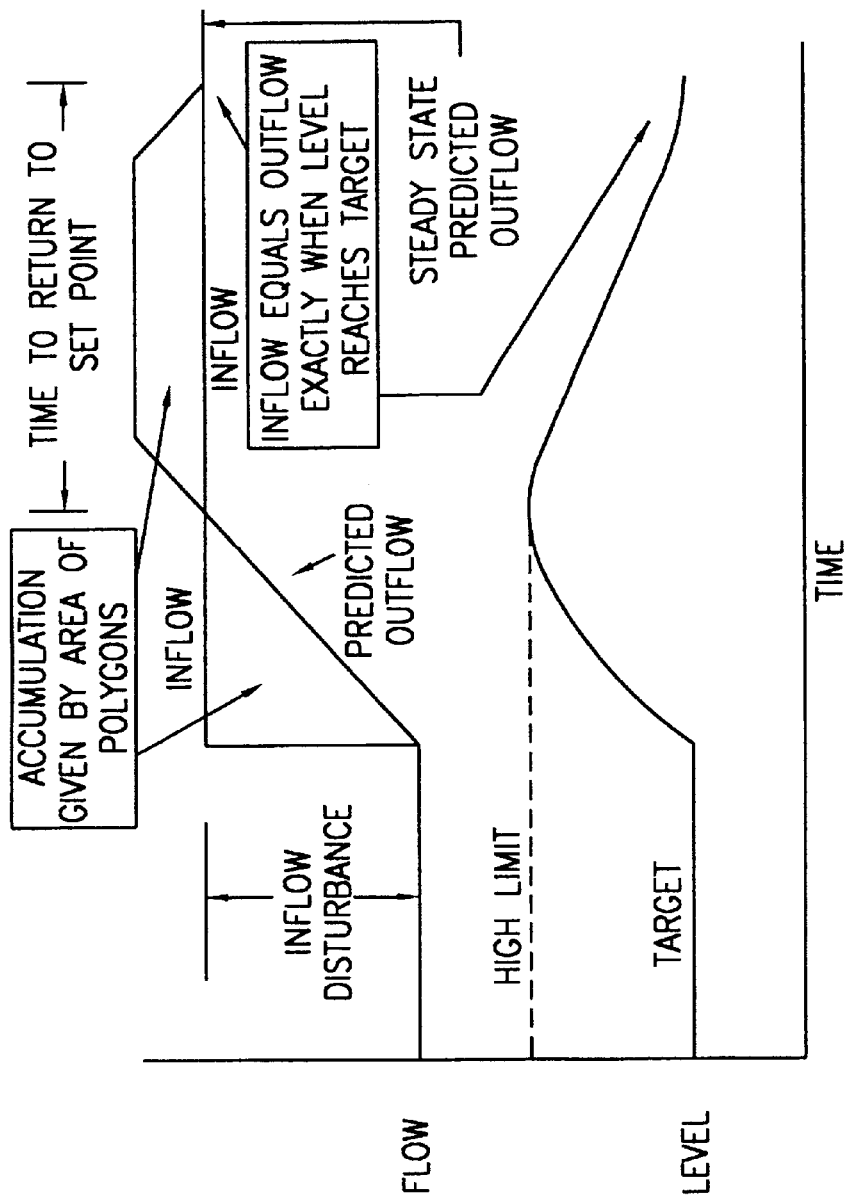
FIGS. 6 is 6A are graphs showing the present invention using advanced level control.

This permits the accumulation or level to be constrained while limiting rate of change of flow to the downstream units. The straight line flow gives optimal control performance as well as predictions of future flow. FIG. 6 shows the predicted flow in a ratio-assisted control with advanced level control. The predicted outflow can be stored in a standard block on the DCS as a series of straight line segments.

Figure 6A:
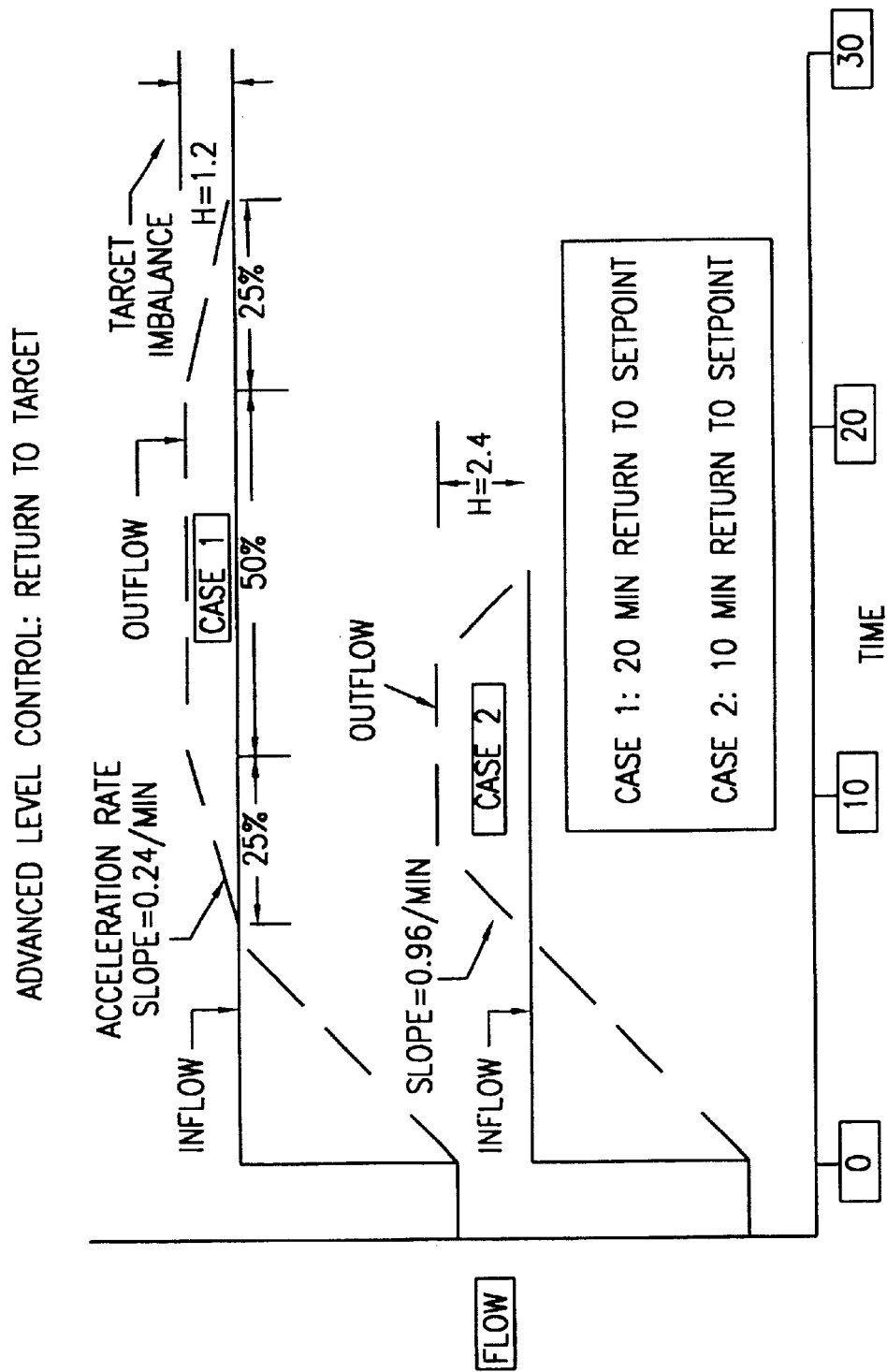

The advanced level control is further exemplified in FIG. 6A, which demonstrates the basic algorithm for returning the level which is used when the level is away from the target but not increasing or decreasing above a certain rate. An engineer specifies as a tuning parameter the number of minutes it will take for the level to be steady, or nearly steady, at the target level.

Given that number of minutes (t), and the volume (V) between the initial and target levels, a flow path for the vessel outflow is established.

The flow path consists of three periods constant imbalance period, and deceleration period. The acceleration period and deceleration period are both defined as a percentage of the total time, with the remaining time going to the constant imbalance period.

As shown in FIG. 6A, the shaded trapezoidal area labeled "Case 1" represents the total volume change required to bring the level to target. Given the shape of the flow path and the time percentages for acceleration and deceleration, the height of the trapezoid or "target" imbalance, balance is directly calculated.

Given the path and target imbalance, there is now sufficient information available to implement the return to target control. The procedure is as follows.

a. An acceleration rate is calculated as [target imbalance/acceleration time]
b. The current imbalance is calculated from the rate of change of level and vessel dimensions.
c. For the acceleration period and the constant imbalance period, the control move is calculated as the lesser of:
   i. [target imbalance−current imbalance]
   ii. [acceleration rate]

This establishes the target imbalance and the flow path shown above.

d. Assuming the 25%–50%–25% split shown above, the beginning of the deceleration period is identified when the volume remaining to the target is ⅙ of the original volume. During the deceleration period the moves are calculated to eliminate the imbalance just as the level reaches target. The calculation for eliminating the imbalance is the same one performed on the left-hand of FIG. 6.

With the entire flow path predicted, any ratio assisted controllers downstream can begin to act as soon as the level begins to change. This is important in feed change to ensure that on specification operation is maintained while reducing the rate of change of all manipulated variables.

Figure 7:
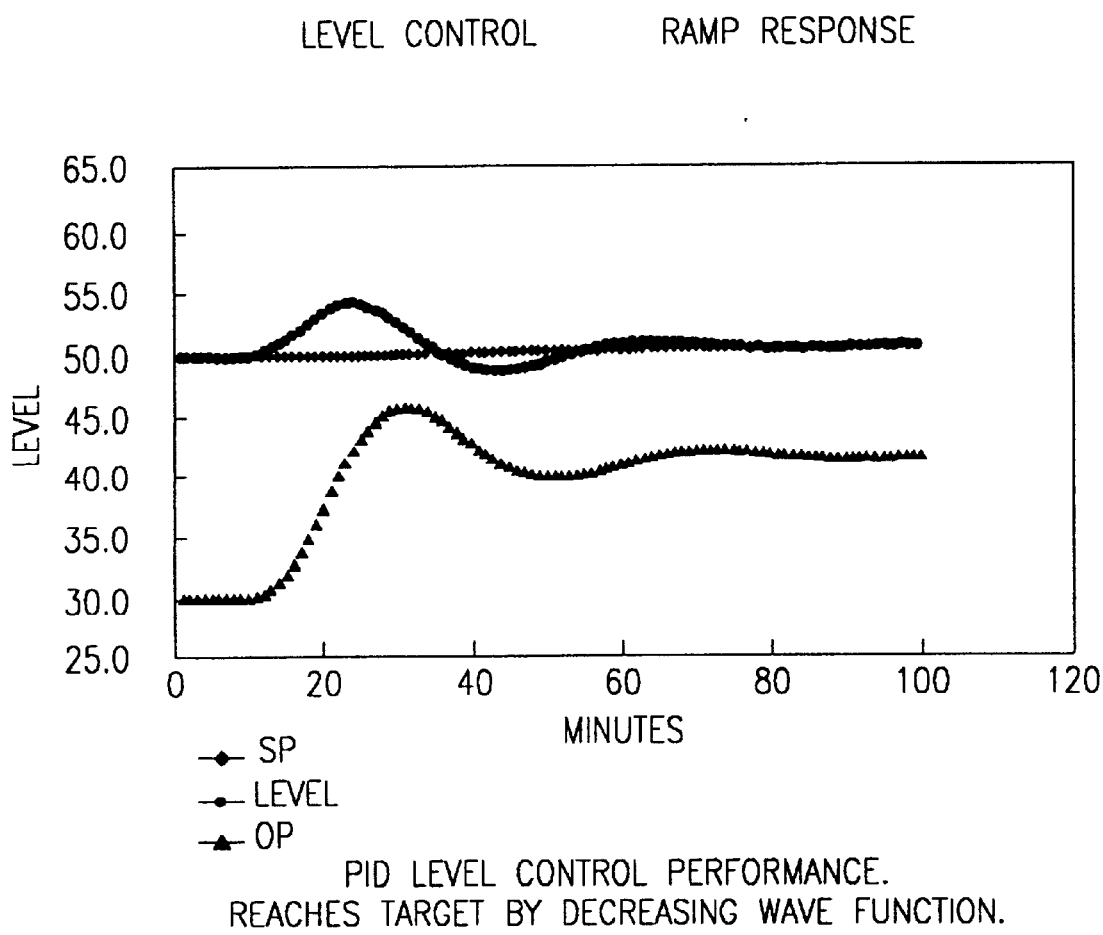
FIG. 7 is a graph showing PID level control performance.

Some multilevel controllers are not able to correctly model the integrating level response, or require trial and error adjustments to work properly. Their performance in this area area is so poor that many control engineers prefer the performance of PID level control to multivariable level control. In order to meet the target following a disturbance material balance principles are used to initiate and maintain a target imbalance, until the level gets near the target. The imbalance is eliminated exactly as the target is achieved as shown in FIG. 6. This avoids the wave pattern that accompanies even well tuned PID controllers. FIG. 7. shows the PID level control performance, where the target is reduced by decreasing wave function.

Figure 8:
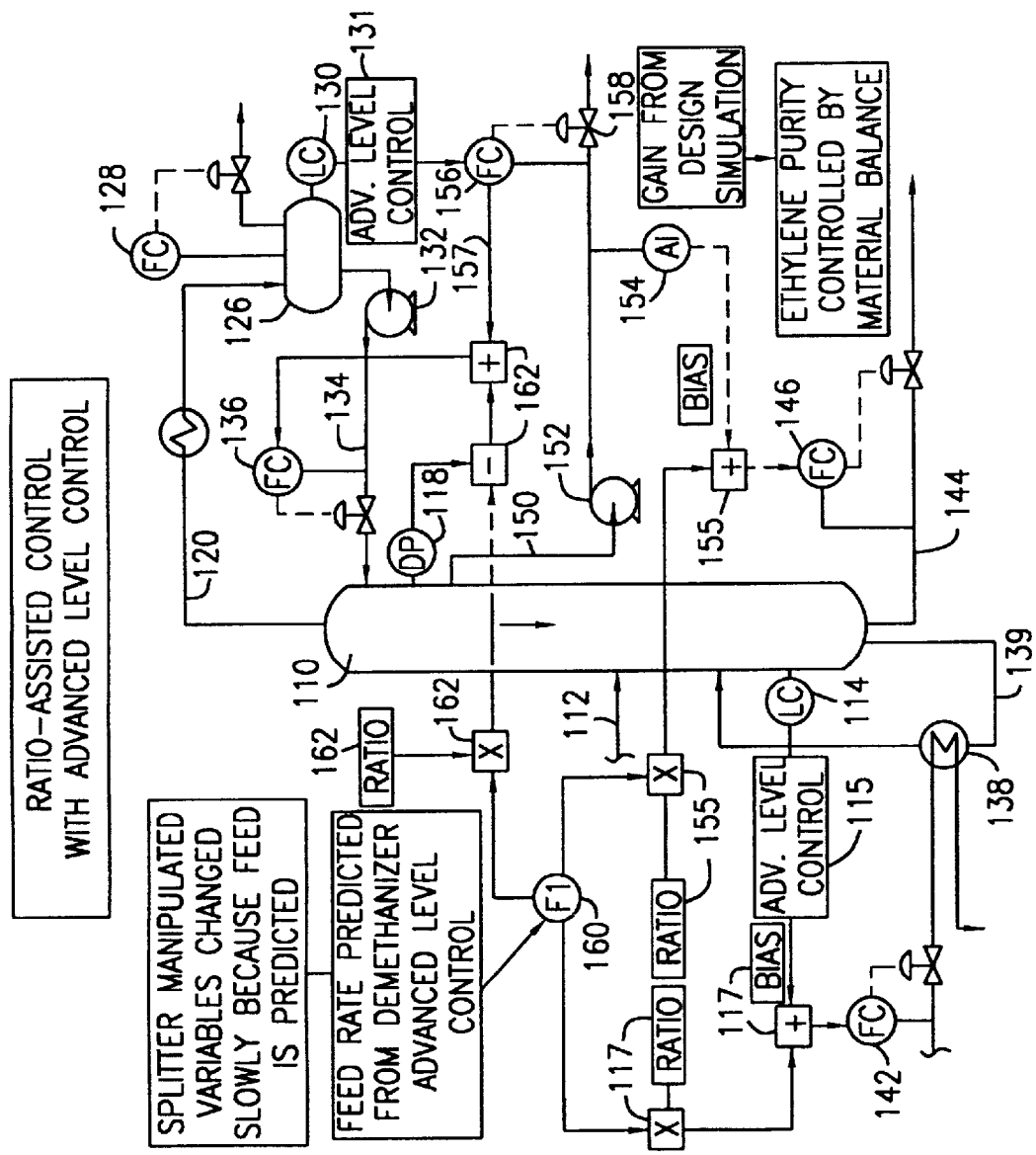
FIG. 8 shows ratio assisted control with advanced level control in the present invention.

As exemplified in FIG. 8, advanced control applications automate some of the functions previously discussed to enhance the performance of the regulatory control system. The result is reduced standard deviation of specification variables with less movement of manipulated variables, thus permitting average operation closer to the equipment limits and performance specifications.

Two applications of advanced control on distillations are described for exemplary purposes hereinbelow systems. In distillation advanced control, the movements of three manipulated variables are coordinated to solve specification control and level control simultaneously. The second is the use of HMB methods to maximize system capacity.

Advanced distillation control is built on the regulatory foundations already described herein. In the case of a C2 splitter, referring to FIG. 8, internal reflux is isolated as the loading variable. In the regulatory configuration, the remaining three variables are assigned as shown in Table 5.

TABLE 5

| Manipulated Variables | Controlled Variables |
| --- | --- |
| Recycle Ethane Flow | Bottom Level |
| Reboiler Duty | Ethylene Purity |
| Ethylene Product Flow | Reflux Drum Level |

With advanced distillation control the 3×3 problem above is solved directly, without linear program to adjust the bias on each of the above ratio-assisted controllers. The equations are solved sequentially and directly.

Referring to FIG. 8 there is shown a control system of advanced level control on a C2 splitter in accordance with the present invention. In FIG. 8 the reference characters for similar equipment to that of FIG. 1 are the same except that in FIG. 8 they have 100 added thereto.

The change in reboiler 138 duty is calculated first. In the basic regulatory system, recycle ethane flow in a line 144 controls ethylene purity and the reboiler 138 duty responds to the resulting change in level. With the advanced control system the bias 117 on reboiler activity is changed directly for ethylene purity control by use of an advanced level controller 115 on the tower bottoms. Solution for the target duty involved one equation and one unknown.

The graph of ethylene purity against recycle ethane flow 13 is regressed and entered into a DCS block. The change in vapor required to achieve target ethylene purity is calculated from the graph. This sets the new bias 117 for the reboiler duty manipulated variable.

Next, advanced level control is applied in both reflux drum and bottoms. The known future change in vapor rate is used to adjust the material balance calculation performed by advanced level control. With the reflux 134 nearly constant, and the vapor changes known, the advanced level control 131 keeps the level within constraints while minimizing changes in product flow.

Additionally, if advanced level control is being used on the upstream towers, then ratio-assisted control can act on the predicted feed rates 160 rather than the actual feed rates. This gives the tower more time to react to feed rate changes, permitting more gradual movement of all variables. Recycle ethane flow 144 is adjusted automatically to feed composition change as part of ratio-assisted control 155.

Another example of the use of advanced control is heat and material balance can also be used to maximize the efficiency of chemical processes by allowing the maximum amount of feed to be added to a system. Since the heat and material balance control addresses constraints while maintaining steady state operation, it is natural to use the heat and material balance tools to maximize feed to a system. The heat and material balance control strategy for capacity maximization has an advantage over the multivariable control strategy: (1) it can provide increased average production through the use of short term accumulation in vessels. (2) Heat and material balance strategy is also favored over conventional multivariable controllers by providing a smaller variation in the rate of change of feed to the furnaces.

Figure 9:
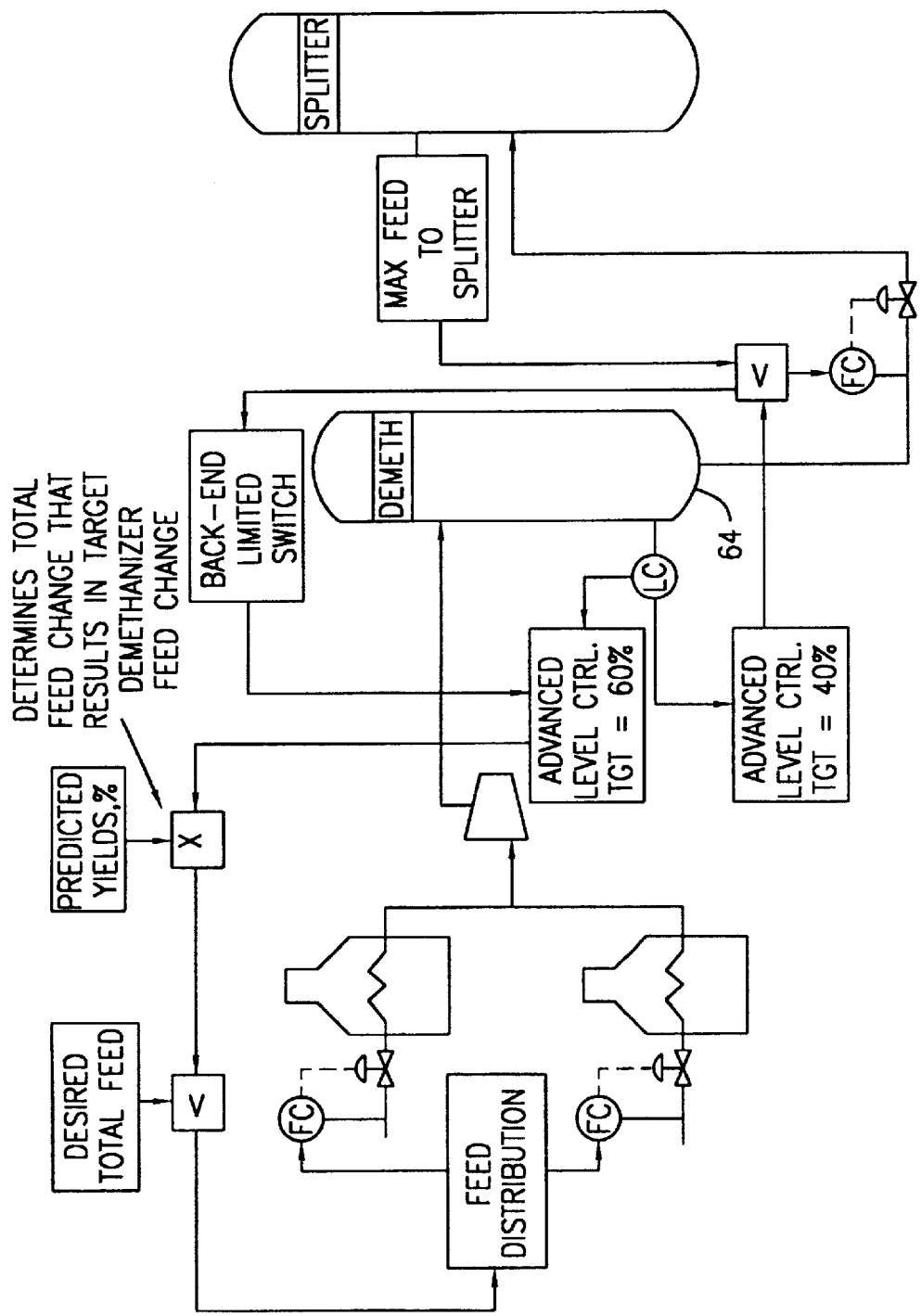
FIG. 9 is a schematic diagram of the present invention showing capacity maximization capacity.

FIG. 9 shows a capacity maximization strategy using the HMB control of the present invention. The basic concept is the same as that of capacity management via a multivariable controller except that the implementation is different.

Each system in the plant is evaluated independently in terms of constraint. A system is considered constrained if the following are all true:

1. Loading variable is limited by equipment constraint.
2. Specification variable(s) are all at the limit, and their respective manipulated variables are all at their limits.
3. The average value of profit related variables such as furnace severity or recycle ethane purity is below minimum value acceptable to operations.

The C2 splitter system, for example has reached its maximum sustainable feed when the following conditions occur simultaneously:

1. Reflux is constrained by equipment capacity.
2. Ethylene purity is at the specification value.

3. Recycle ethane flow cannot be increased any further because of a constraint such as heat exchanger capacity or ethylene loss in the bottoms stream.

The only degree of freedom remaining at this point to maintain on-specification operation is to reduce the feed. A flag is set for each system when its feed is constrained.

This approach is different from the multivariable approach since the multivariable controller immediately moves to reduce the feed to the furnaces, using a prioritization to divide the total feed change among selected furnaces. The heat and material balance system, however, does not have to reduce the total feed to the furnaces as quickly. Instead, heat and material balance allows material to accumulate in selected vessels throughout the plant. As shown in FIG. 9 the level of some intermediates drum or tower in the plant is controlled by the total feed, using the advanced level control algorithm. Total furnace feed is reduced gradually as the level in the intermediate vessel increases. When the downstream constraint is relieved the accumulated material in the intermediate vessel 64 is available to immediately increase feed to the downstream systems and ultimately product rates. The accumulated material represents additional capacity beyond what can be achieved with multivariable controllers that do not typically use accumulation as a tool.

The extra capacity resulting from this strategy is multiplied every time the inventory of the intermediate vessel 64 builds and drains. For example, the change in refrigeration capacity from day to night or from sunshine to clouds or drizzle on a hot summer day creates opportunity to safely and smoothly increase production as constraints become eased.

Possibly even more important is the reduced rate of change of feed to the furnaces made possible by this special application of advanced level control. Furnace severity control is difficult even at constant feed rate, with difficult process measurements and rigid constraints. It is even more difficult when the feed changes. All furnace models will have to be nearly perfect to maintain firebox conditions, steam to feed ratios, pass balancing and severity at their target ranges. Furthermore, the tube metal temperature prediction comes into question as the firing rate begins to vary. Without constant firing, the value of the manual pyrometer reading is diminished. The furnace could well be in the state of adjustment at the time of the reading.

The method described above for returning a level to the permanent target can be used more generally to change liquid inventory from any initial volume to any temporary target volume. In the capacity maximization algorithm, a large vessel or tower bottom section (called the storage vessel) can be used and an intermediate storage tank between the front end and the back end of the plant. During normal operation, the target level for the storage vessel would be set at 40% or thereabouts. When the equipment downstream of the vessel is limited, a 'limited' flag is set, and the feed from the storage vessel to the downstream equipment is decreased.

When the 'limited' flag is set, the capacity maximization routine automatically changes the storage vessel target from 40% to 60% and allows material to gradually build using advanced level control. With the outflow from the storage vessel being limited by the downstream unit, the level of the storage vessel is now controlled by the feed to the plant. In the case of the ethylene plant, the storage vessel might be the demethanizer bottom section. The required decrease in feed to the demethanizer bottom (FIG. 9) is multiplied by a furnace yield factor to determine the reduction in fresh feed rate required for control of the demethanizer bottom level. With the level in the demethanizer bottom level building from 40% to 60%, the feed does not have to be reduced as quickly as if the demethanizer bottom level were held constant.

When the downstream limit is relieved later on, the target level for the storage vessel is changed back to 40%, with the extra feed for the downstream unit being immediately available. Each time the inventory changes from 40% to 60% and back to 40% the total production of the plant is increased by the volume of material contained between 40% and 60% level of the storage vessel.

In many types of refinery and petrochemical plants, there is a reactor at the front end of the plant and a distillation system at the back end of the plant to separate the products of the reactor. In many of these back-end distillation systems, the capacity is limited by heat removal via either cooling water or refrigeration. In warm climates, the heat removal constraint is affected by day-to-night temperature changes and by intermittent periods of clouds and rain that may occur on a summer's day. During a warm summer day with two or three rainstorms and intermittent periods of clouds and sunshine, the level of the storage vessel could be changed from 40% to 60% and back many times during the course of the day. The resulting production increase obtained using the method described above is greater than what can be achieved if levels are held constant.

An additional benefit of allowing material to accumulate is that rate of change of feed to the front end reactor does not have to be as fast as the rate of change of feed from the storage vessel to the limited unit downstream.

Thus, the heat and material balance strategy is theoretically capable of greater capacity than the typical multivariable control application, while at the same time reducing variation of feed rate to the furnaces.

EXAMPLE 1

Figure 10:
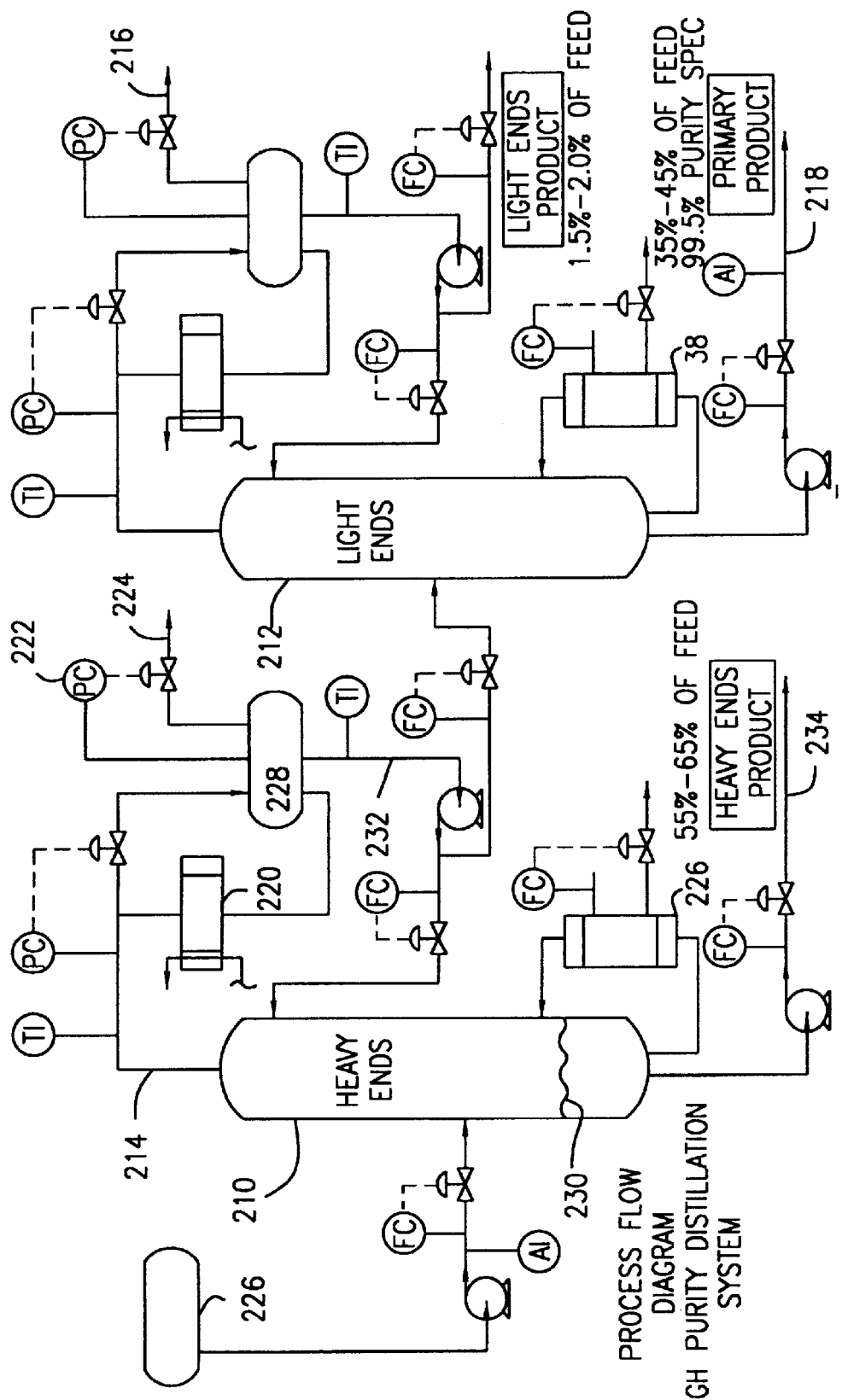
FIG. 10 is a schematic diagram of the present invention showing a distillation system process flow diagram.

A test of the heat and material balance strategy with the basic regulatory configuration and operator control of composition and constraints has been performed on a high-purity distillation system. The system separates both heavy ends and light ends from a primary product in a two-tower system. A sketch of the system is shown in FIG. 10, showing distillation towers 210 and 212.

Feed to the distillation system in a line 226 is a liquid mixture of close-boiling hydrocarbons divided into three groups: lights, heavies and primary component. Table 6 gives the approximate range of feed compositions during the test period.

TABLE 6

| Component | Approximate % of Feed |
| --- | --- |
| Lights | 1.5–2.0 |
| Primary Component | 35.0–45.01.5 |
| Heavies | 55.0–65.0 |

The feed goes first to a heavy ends removal tower 210. The distillate from tower 210 in a line 214 becomes the feed to tower 212, where the light ends are rejected in an overhead stream 216, and the primary product is recovered at the bottom in a line 218.

The primary product specifications are for less than 0.5% mole (5000 ppm) total impurities. The objectives of the distillation system are to maximize recovery of the primary product at a given feed rate while maintaining primary product purity. During the test period the system was limited by condensing capacity on both towers. Disturbances to the system included feed rate and feed composition changes.

The heat and material balance configuration is shown in Table 7.

TABLE 7

| Heat & Material Balance variable | Tower A | Tower B |
|---|---|---|
| Loading Variable | Internal Reflux | Reboiler Duty |
| Product Specification Variable | Heavies on Product | Lights in Product |
| Specification Controlling Variable | Tower 210 Bottoms flow | Tower 212 Distillate Flow |
| Inventory Control | Tower 210 Distillate Flow | Tower 212 Bottoms Flow |

Tower 210 pressure was limited by design pressure and protected by a relief valve and backup pressure controller that vented the flare. Whenever the heat exchanger 220 as unable to condense the entire tower overhead, then the vent pressure controller 222 would open to flare via a line 224.

Figure 11:
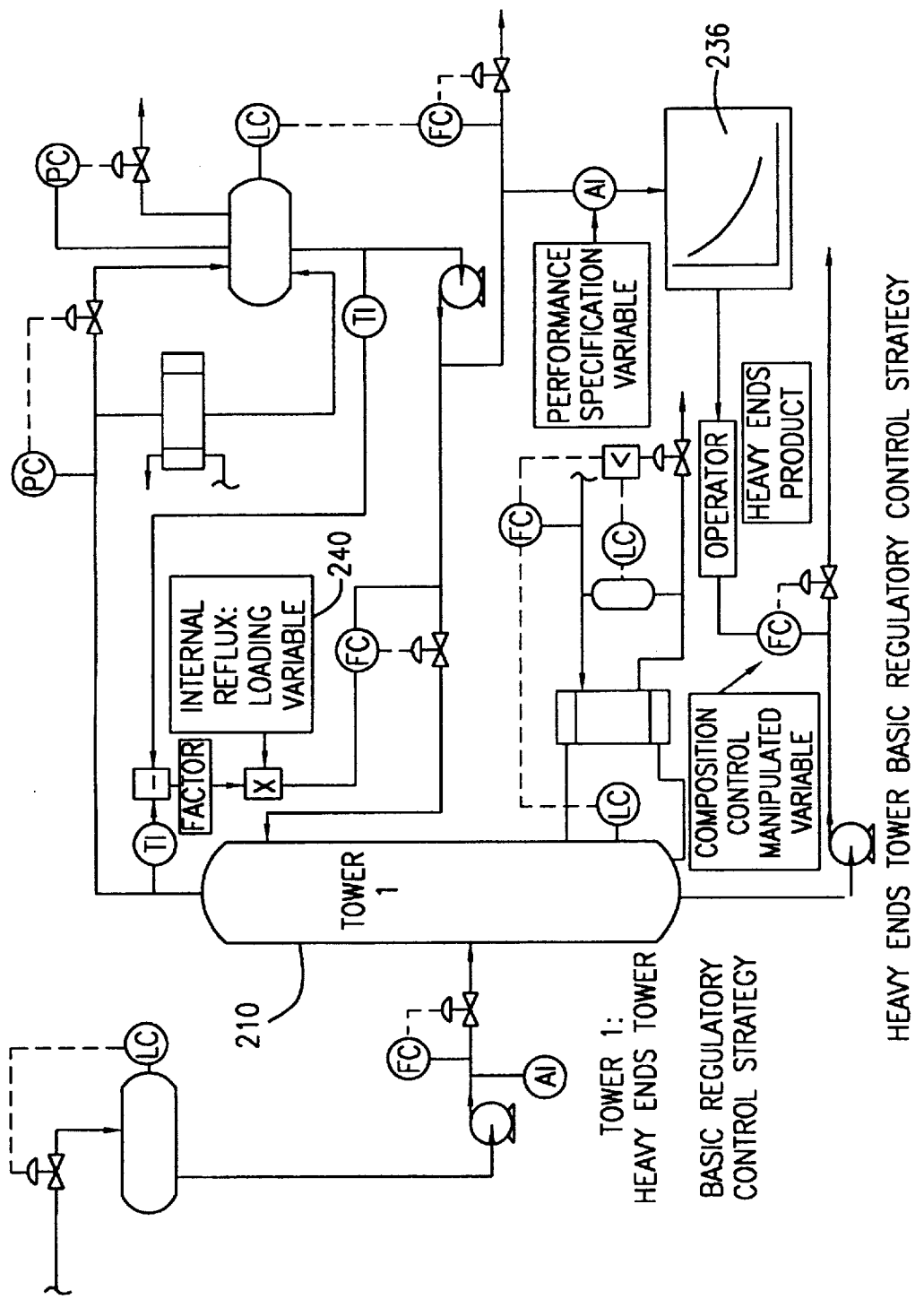
FIG. 11 is a schematic diagram of the present invention showing heavy ends tower basic regulatory control strategy.

The system went through an initial startup phase following construction. Originally, tower 210 was commissioned with conventional strategy, with the reflux being used as the manipulated variable for heavy ends rejection. Reboiler 226 duty was held constant, with the reflux drum 228 and bottoms level 230 controlled by their respective product streams 232, 234. This strategy led to frequent venting episodes during the day as the cooling water temperature increased resulting in off specification production major loss of product to the vent and erratic cycling behavior. The heat and material balance strategy was installed to give the operatic separate handles for composition control and for constraint management. Internal reflux was selected as the loading variable 240 for tower 210. The design simulation was used to generate a graph 236 of product purity against heavy ends product flow, which was posted in the control room. FIG. 11 shows the controls for tower 210.

Figure 12A:
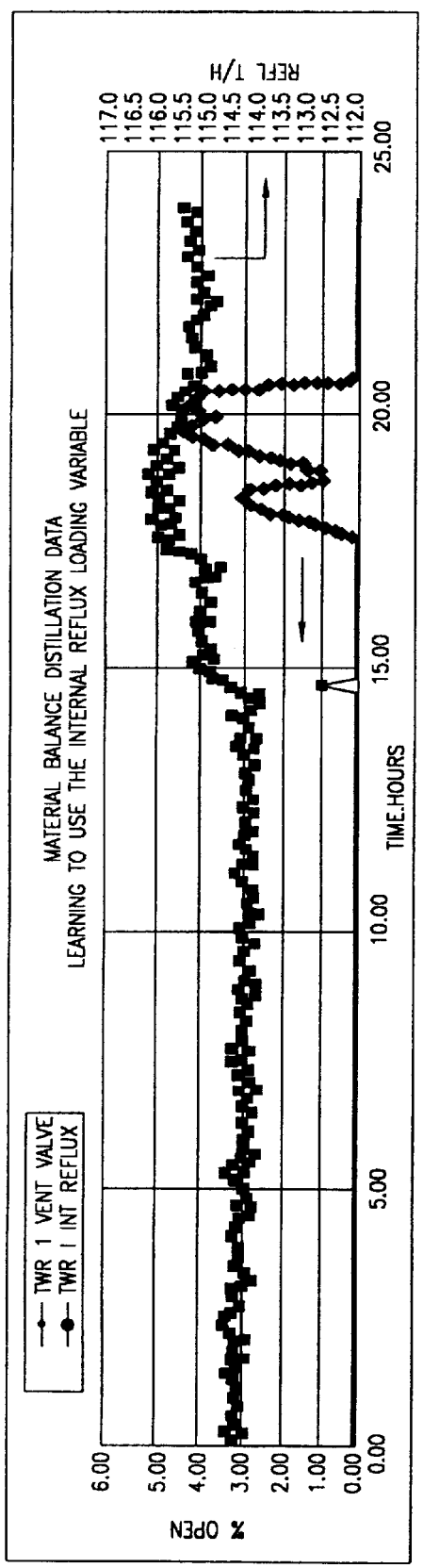
FIGS. 12a and 12b are schematic diagram showing the light ends increase and the regulatory control strategy.
Figure 12B:
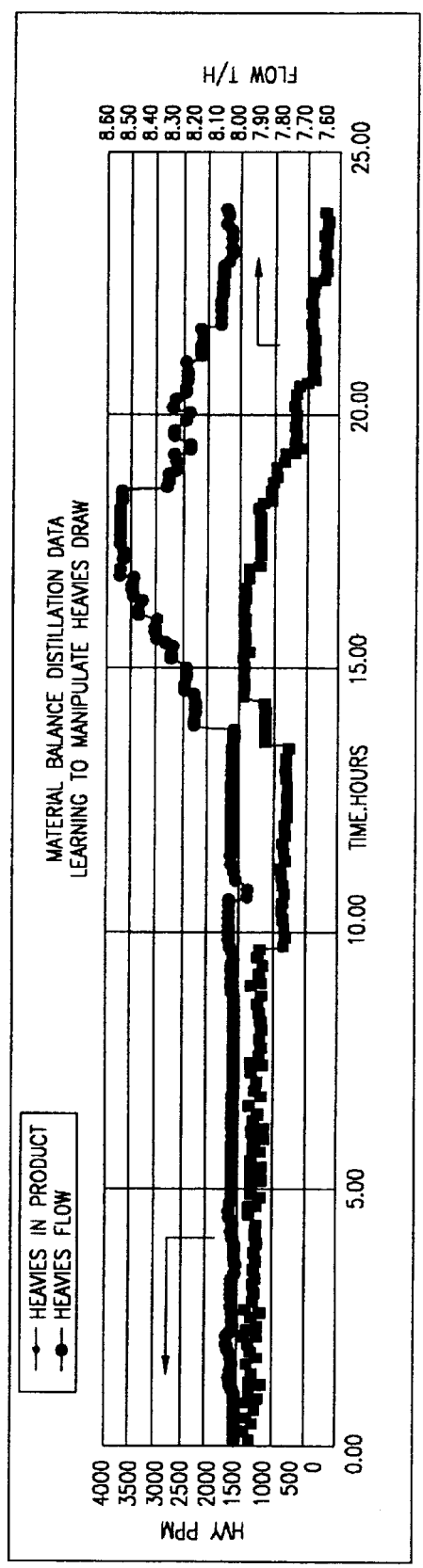

Almost immediately the operators gained control over the condenser constraint and the product purity. FIGS. 12a and 12b are 24 hour trends of plant data that show the operators initial efforts at learning the new control system. As shown in FIG. 12a, the operator increased the internal reflux to 116 tons/hr which resulted in the venting opening slightly. The operator then reduced the internal reflux just enough to get the vent to close. Within a few days the operators had identified the maximum possible reflux without venting and learned how to gradually change the heavy ends product flow to control heavy ends impurity in the product. FIG. 12b shows the initial experimentation with the heavies draw and the heavies impurity in the primary product.

In the regulatory mode of operation, the internal reflux was left nearly constant all day, at the rate which the heat exchanger could have achieved during the warmest part of the day. The heat and material balance operating strategy is what enabled the operators to isolate constraint management from the composition control. Keeping internal reflux constant also ensures constant molal overflow on the trays, maximizing tower 210 efficiency.

The other major advantage for the operator with heat and material balance is that there is almost never a concern about the composition control handle becoming constrained. This gives the operator confidence that he will not have to retract a composition control move because of a constraint.

Because of the way heat and material balance addresses degrees of freedom, if the heavy-ends flow becomes constrained for some reason with the primary product off specification then there is no other choice but to cut feed.

Figure 13:
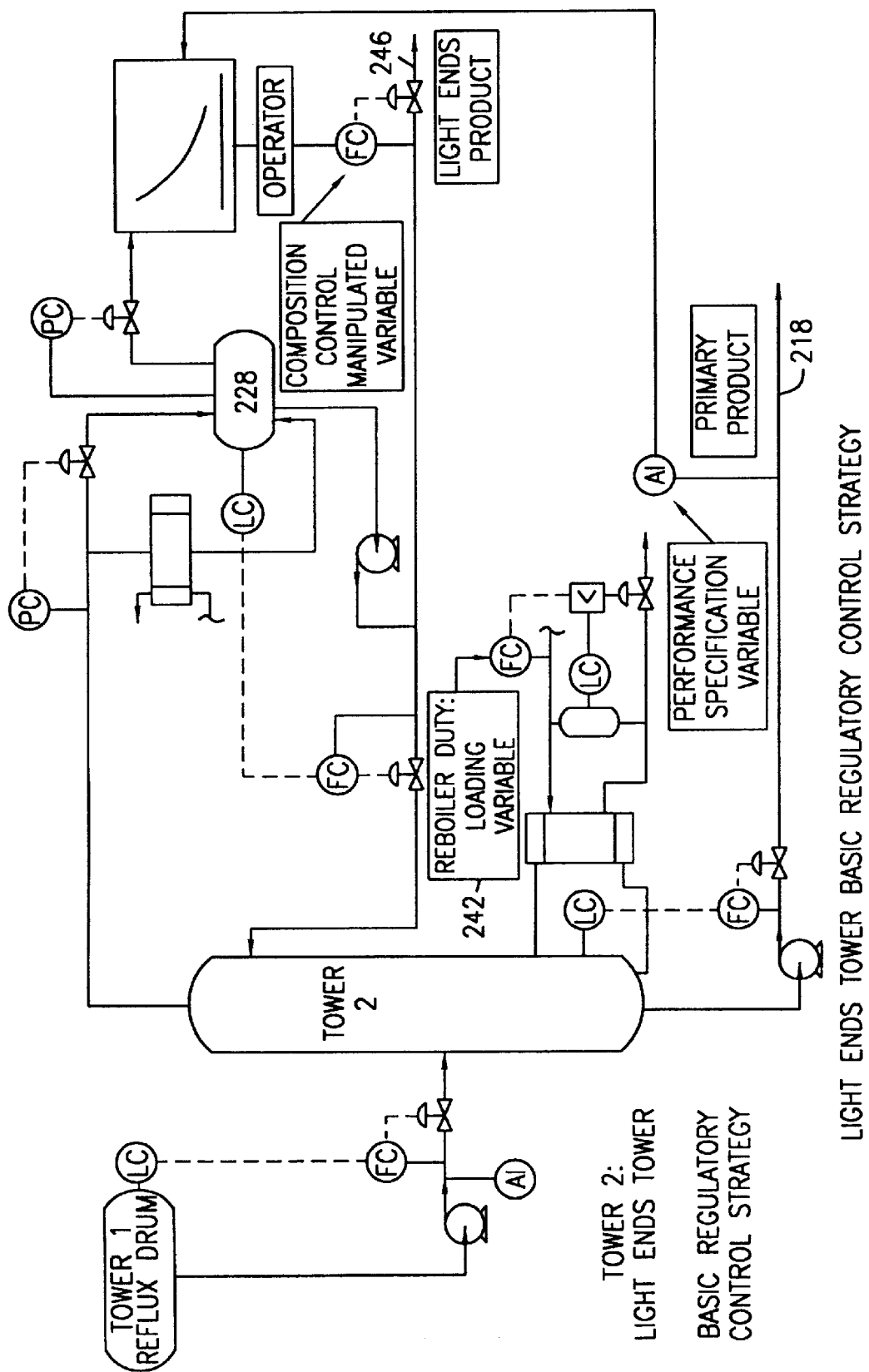
FIG. 13 is a graph showing the light ends tower basic regulatory control strategy.
Figure 14A:
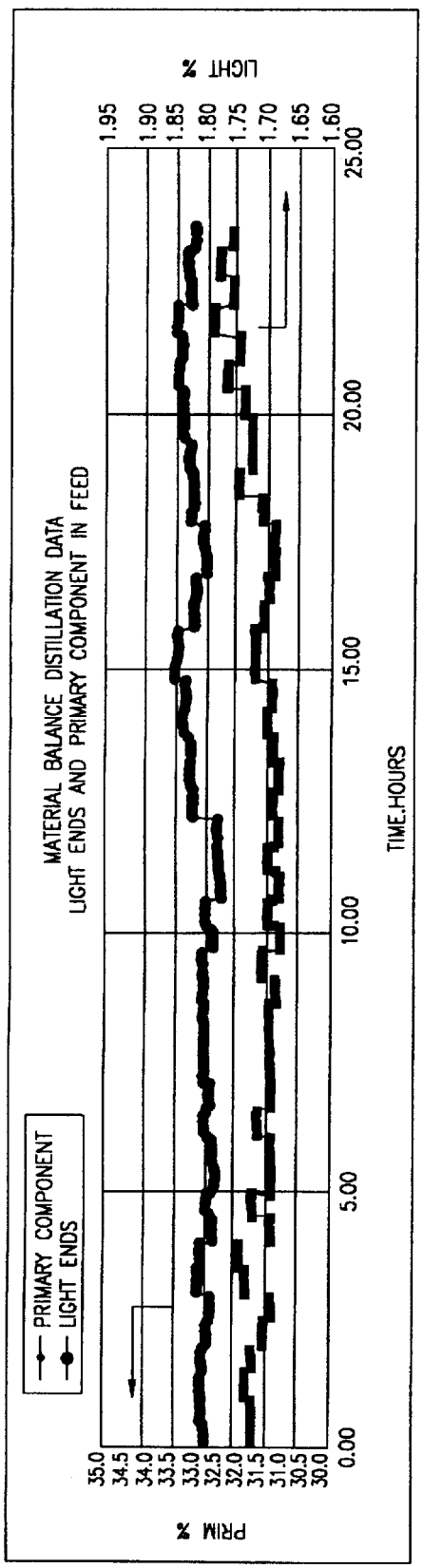
FIGS. 14 a–d is are graphs showing the rate composition increase and operator's response in the present invention.
Figure 14B:
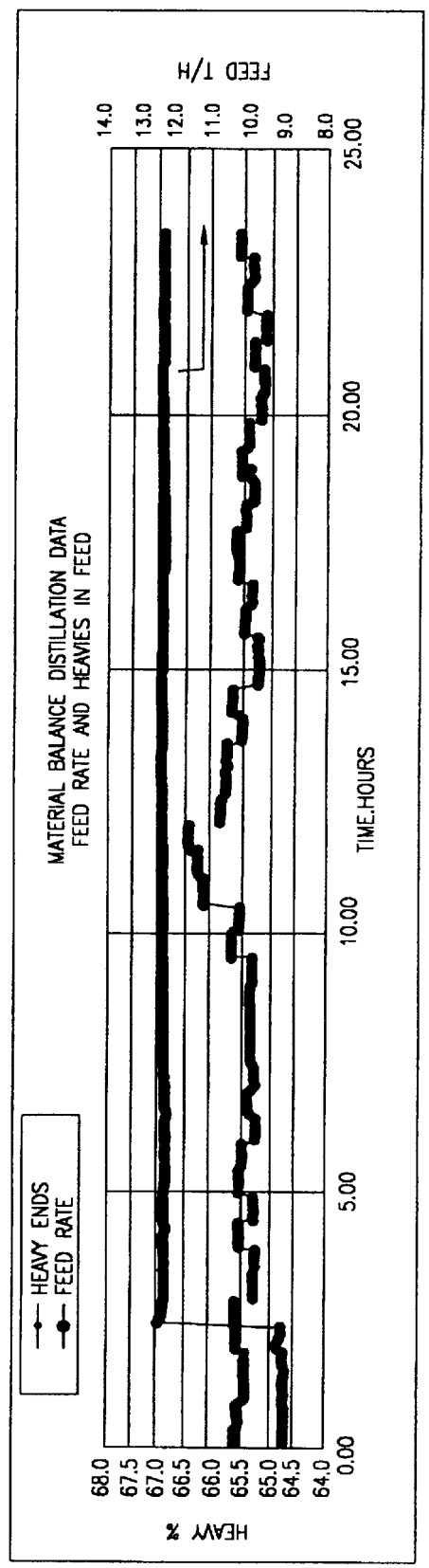
Figure 14C:
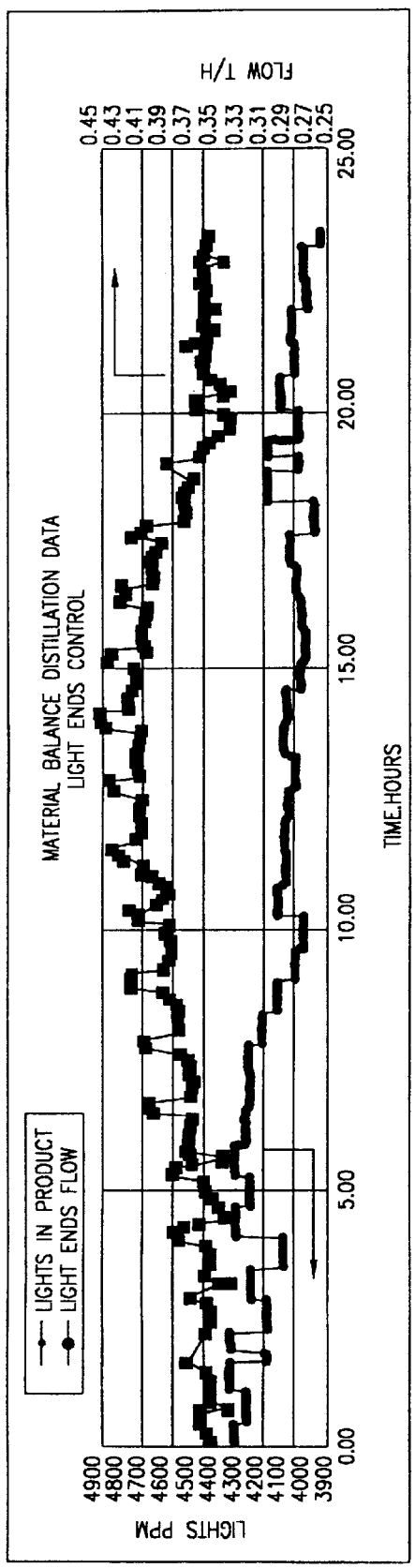
Figure 14D:
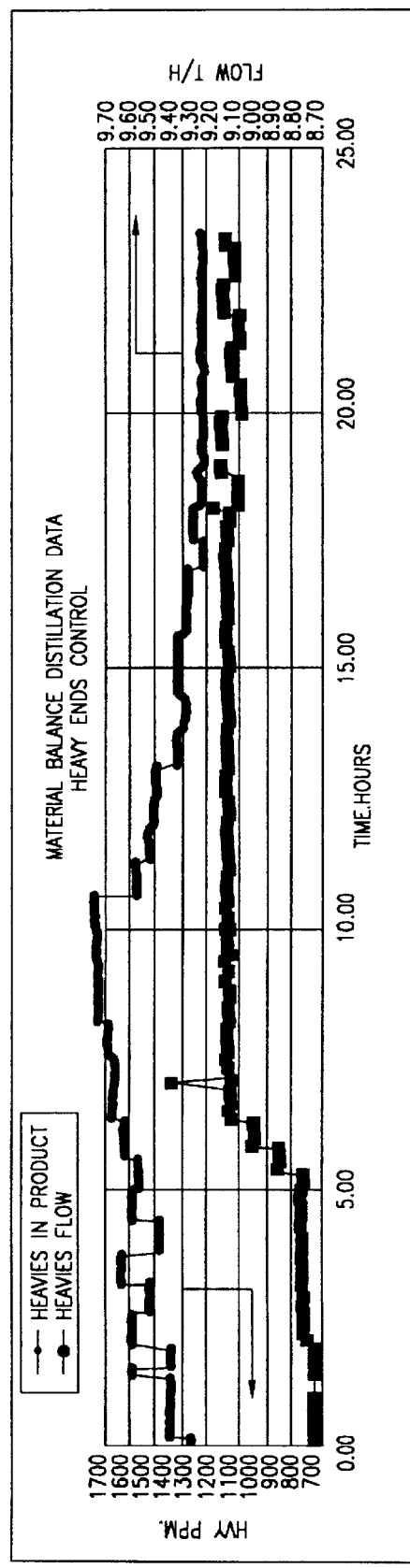

FIG. 13 shows the control strategy for tower 212, the light ends removal tower. For tower 212, reboiler duty 242 was selected as the loading variable, with reflux controlling the level of the reflux drum 228 and light ends in the primary product being controlled by light ends product draw 246.

FIG. 14 shows the operator's response to a feed rate change at nearly constant feed composition. FIGS. 14a and 14b both show the feed rate and composition. FIG. 14c shows the response of the light ends tower 210 composition control and FIG. 14d shows the heavy ends tower performance. FIG. 14a shows some spikes on the light ends product rate, which are not actual moves by the operator. The important point of all of the FIGS. 14a–d is not so much the preciseness of the control, but the observation of how the process shifts from one steady state to another under constrained conditions, always satisfying the degree of freedom. FIGS. 14a–d show the potential benefit of adding ratio-assisted control to the basic regulatory strategy.

Figure 15A:
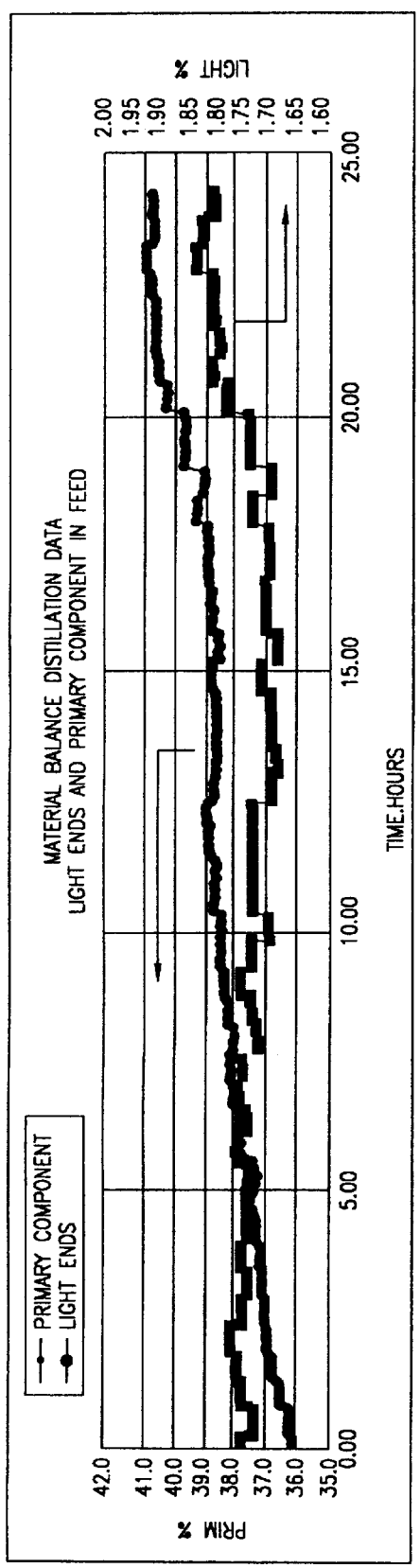
FIGS. 15 a–f are graphs showing the feed rate increase any response composition change and response to condenser restraint.
Figure 15B:
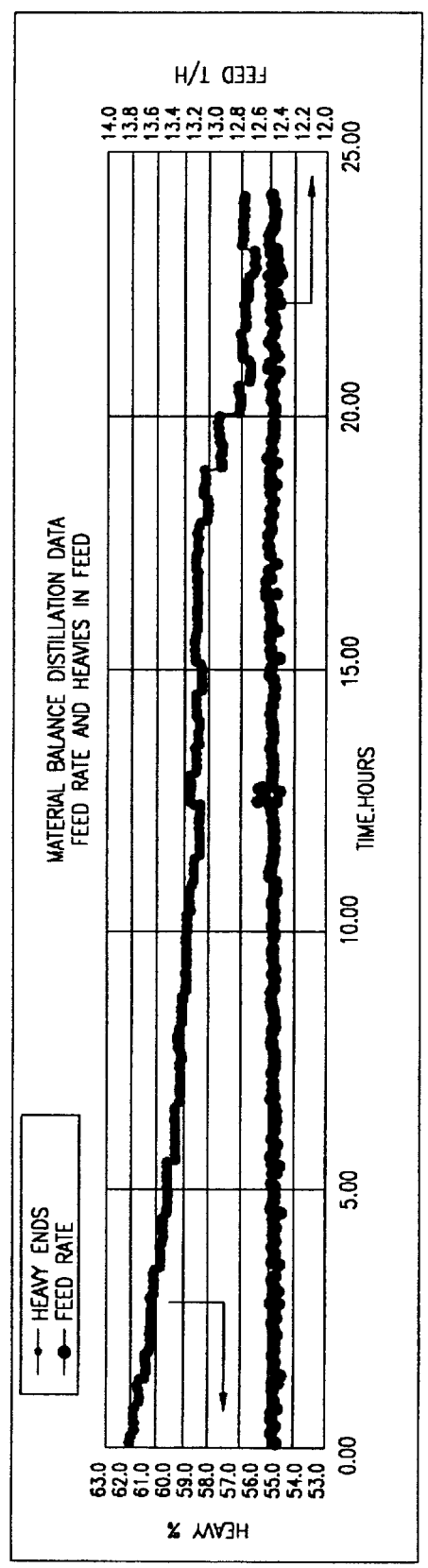

FIGS. 15a–f show an example of response to feed composition changes under constrained conditions. In FIG. 15 the heavies in the feed are decreasing while the primary component is increasing. FIG. 15d gives an idea of the potential value of using ratio-assisted control, including the use of the feed analysis in the ratio calculation. As the heavy ends in the feed decrease from 62% to 57%, the operating reduced the heavy ends product rate from 9.2 ton/hr to 8.9 ton/hr. Even with the vent opening at midday the operator reduced internal influx from 116 ton/hr to 112 ton/hr an relaxes.

Since the strategy is keeping a relatively constant heat and material balance it can remain on-line during analyzer calibrations unlike many multivariable control applications which must be turned off because they are based on an empirical model using the product analyzer. The multivariable controller would then have too take several hours of operation to re-establish its predictions following the outage. Heat and material balance would continue to maintain heat and material balance ratios during the outage with ratio-assisted control.

Figure 15E:
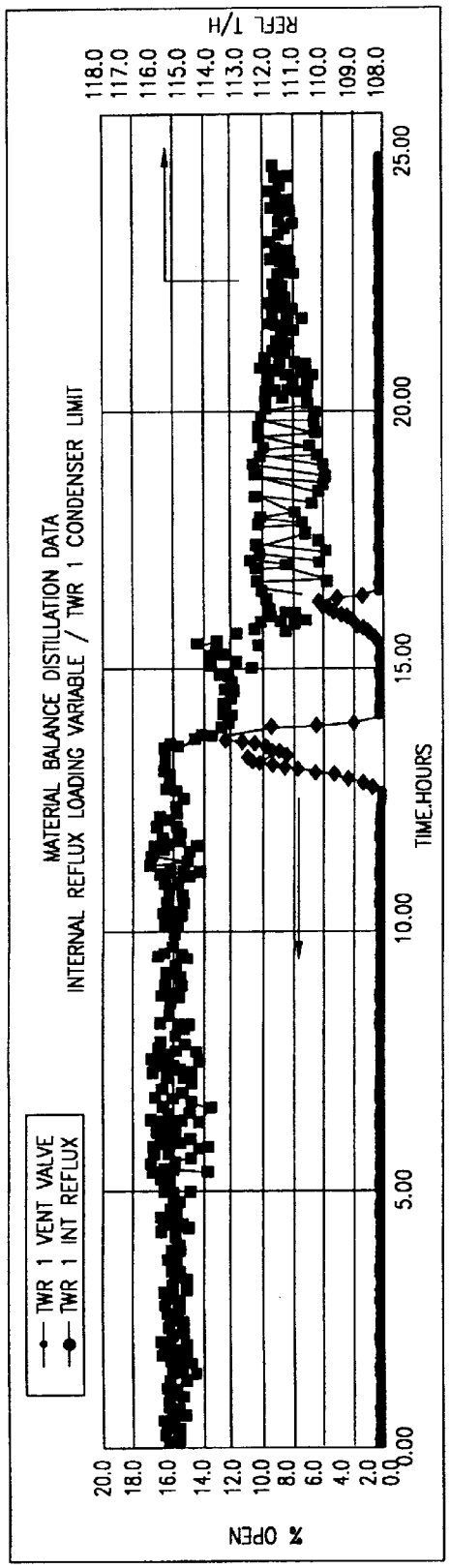
Figure 15F:
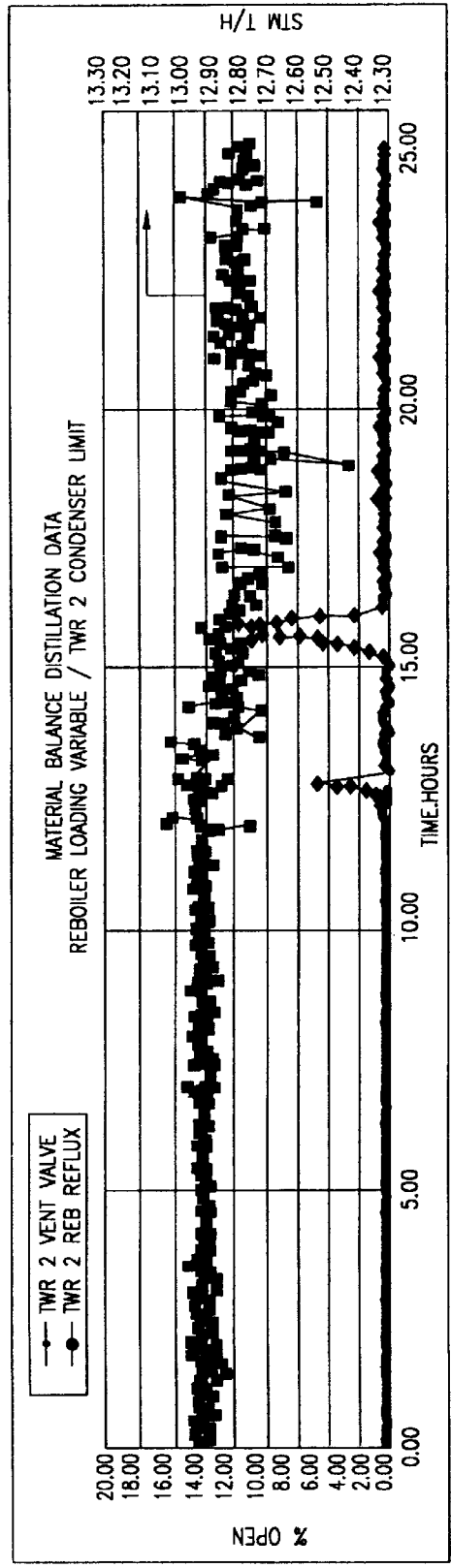

FIGS. 15e, and 15f shows the operator responding to the constrained heat exchanger 226 situation in towers 210 and 212 by adjusting the variables in each case.

Many variations of the present invention will suggest themselves to those skilled in the art. All the variations are within the full intended scope of the appended claims.

The above mentioned patents and publications are hereby incorporated by reference.

What is claimed is:

1. A method for controlling a chemical processing system having operating variables, said method comprising:
   a) selecting a loading variable from said operating variables, said loading variable being directly related to an external source of energy input into the system and being capable of managing equipment load within said system;
   b) selecting a performance specification variable which is required to be kept within a defined target at all times during operation of said system;
   c) selecting a manipulated variable having a mass/balance relationship to said performance specification where said manipulated variable is not said loading variable; and d) controlling said manipulated variable to maintain said performance specification variable with said defined target.

2. The method of claim 1 wherein said loading variable is maintained to keep a nearly constant load on the system.

3. The method of claim 1 wherein the chemical processing system is an ethylene splitter.

4. The method of claim 3 wherein the loading variable is internal reflux and the manipulated variable is ethane flow.

5. The method of claim 4 wherein ethane flow is adjusted according to a simple plot of ethylene purity versus ethane flow.

6. The method of claim 3 further comprising using an advanced level control comprising ratio-assisted control effected by adjusting a bottoms level of the splitter.

7. The method of claim 6 wherein the advanced level control uses level measurement and vessel dimensions to control accumulations and material imbalances.

8. The method of claim 3 wherein the magnitude of a feed change is calculated as a magnitude of change in product rate required before a constant level is established; and the accumulation between current time and time at which constant level is reached.

9. The method of claim 8 comprising the additional step of using a bias and wherein the manipulated variable target equals the (ratio)·(feed)+bias.

10. The method of claim 9 wherein the ratio used for ethane flow calculation is based on the product of feed rate multiplied by ethane concentration in the feed.

11. The method of claim 1 further comprising using advanced regulatory control to respond to changes in a feed rate wherein advanced regulatory control is comprised of ratio-assisted control wherein the manipulated variable is equal to (ratio) (feed)+bias.

12. The method of claim 11 wherein the ratio used for ethane flow calculation is based on the product of feed rate multiplied by ethane concentration in the feed.

13. The methods of claim 1 wherein advanced level control is used to maximize the efficiency of chemical process by allowing the maximum amount of a feed to be added to a system.

* * * * *